United States Patent
Benkovic et al.

(10) Patent No.: US 6,413,751 B1
(45) Date of Patent: Jul. 2, 2002

(54) DNA ADENINE METHYLTRANSFERASES AND USES THEREOF

(75) Inventors: Stephen J. Benkovic, State College, PA (US); Anthony Berdis; Irene Lee, both of Shaker Heights, OH (US); Lucy Shapiro, Stanford, CA (US); Rachel Wright, Menlo Park, CA (US); Craig Stephens; Lyn Sue Kahng, both of Mountain View, CA (US)

(73) Assignees: The Board of Trustees of the Leland Stanford Jr. University, Stanford, CA (US); The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/269,137

(22) PCT Filed: Sep. 17, 1997

(86) PCT No.: PCT/US97/16593
§ 371 (c)(1),
(2), (4) Date: Jul. 19, 1999

(87) PCT Pub. No.: WO98/12206
PCT Pub. Date: Mar. 26, 1998

Related U.S. Application Data

(60) Provisional application No. 60/020,089, filed on Sep. 19, 1996.

(51) Int. Cl.$^7$ .............................. C12N 9/10; C07H 21/04
(52) U.S. Cl. ....................................... 435/193; 536/23.2
(58) Field of Search ...................... 435/193; 536/23.2

(56) References Cited

PUBLICATIONS

Berdis, A. et al., Proc. Natl. Acad. Sci. USA, vol. 95, pp. 2874–2879, Mar. 1998.*
Palmer and Marinus, Gene 143:1–12(1994).
Zweiger et al., J. Mol. Biol. 235:472–485, 1994.
Stephens et al., Proc. Natl. Acad. Sci. 93:1210–1214, 1996.
Stephens et al., J. Bacteriol, 177:1662–1669, (1995).
Wright et al., Genes and Development 10:1532–1542(1996).
Bazer et al., Nucleic Acids Res. 19:5081(1991).
Ohsuka et al., J. Biol Chem. 260:2605–2608(1985).
Rossolini et al., Mol. Cell. Probes 8:91–98(1994).
Matteucci et al., J. Am. Chem. Soc., 103:3185–91 (1981).
Smith and Waterman (1981) Adv. Appl. Math.2:482–89.
Needleman and Wunsch(1970) J. Mol. Biol.48:443–453.
Pearson and Lipman (1988) Proc. Natl. Acad. Sci. (USA)84:2444–2448.
Gibler U. and Hoffman, B.J. Gene 25:263–269(1983).
Benton and Davis, Science 196:180–182(1977).
Grunstein et al., Proc. Natl. Acad. Sci. USA/. 72:3961–3965(1975).
Needham–VanDevanter, D.R., et al., 1984, Nucleic Acids Res., 12:6159–6168.
Pearson J.D. and Regnier FE., 1983, J. Chrom., 255:137–149.
Gillman and Smith (1979), Gene, 8:81–97.
Roberts et al., (1987), Nature, 328:731–734.
Berger and Kimmel, Guide to Molecular Cloning Techniques, Methods in Enzymology, vol. 152: Academic Press, Inc. P 307–316, 1987.
Froehler et al., (1986) Nucleic Acids Res., 14:5399–5407.
Sinha et al., (1984) Nucl. Acids Res. 122:4539–4557.
Gall and Pardue (1969) Proc. Natl. Acad. Sci. USA 63:378–383.
John et al., (1969) Nature 223:582–587.
Kwoh et al., (1989), Proc. Natl. Acad. Sci. USA 86:1173–1177.
Guatelli et al., (1990) Proc. Natl. Acad. Sci. USA 87:1874–78.
Lomell et al., (1989), J. Clin. Chem., 35:1826–31.
Landegren et al., (1988), Science 241:1077–1080.
VanBrunt (1990) Biotechnology, 8:291–294.
Barringer et al., (1990), Gene 89:117–122.
Scoknanan and Malek (1995) Biotechnology 13:563–564.
Angerer et al., Methods Enzymol., 152:649–661(1987).
Kohler and Milstein (1975) Nature 256:495–497.
Huse et al., (1989) Science 246:1275–1281.
Ward et al., (1989) Nature 341:544–546.
Malim et al. (1989) Nature 341–544–546.
Trono et al., (1989) Cell 59:113–120.
Clandrasegaran et al., Gene 70:387–392, 1988.
Hynes et al., Gene 78:111–120, 1989.

* cited by examiner

Primary Examiner—Ponnathapu Achutamurthy
Assistant Examiner—Malgorzata A Walicka
(74) Attorney, Agent, or Firm—McDonnell Boehnen Hulbert & Berghoff

(57) ABSTRACT

The present invention relates to the isolation and sequencing of a novel class of methyltransferase genes, including the methyltransferase gene from *Rhizobium meliloti, Agrobacterium tumefaciens, Brucella abortus,* and *Helicobacter pylori.* The invention further comprises efficient methods of assaying methyltransferase activity.

5 Claims, 11 Drawing Sheets

FIGURE 1. Rhizobium meliloti methytransferase gene sequence

DNA sequence 1698 b.p. GCAGTGATGGCG ... CGCCTTCGACAT linear

1/1                                   31/11
GCA GTG ATG GCG GCC TGG GCT GCA AGC TCC GTC CGT GTC AGC GCC TGG CCG CCC ATC AGA
61/21                                 91/31
GCG GGC AGC ATG TTT GCG CGT GCG GGA TCG CCG ATC AAC GAG CCG ATC AGA GCT ATG TCC
121/41                                151/51
GGG CCT TCC TTC ATA CTT CGA TGA TAA TCG AAG TAT CGC GGA CGG GCA AGA CCC GGA TCG
181/61                                211/71
GCG GCG CCT GGA CGA TGA CTC CTG CGG CGA CGC AAA TTT TTC CGG CGC CTT CAG GCT TTG
241/81                                271/91
GTA ACC ATC TTC GGT AAC CAT AAG CCT ATC GTC AGT CCG AGT AAG CGT ATT TGC GAG TTG
                                      331/111
CCA ATG TCA TCA GTT GTT TCG CTT GCC GAA ATC TCC CGT GCC GCC CGT CCG CTG AAC TGG
361/121                               391/131
CTG GAC AGC ATC ATC AAG GGA GAT TGC GTG GCC GCG CTG AAC GCG CTT CCC GAT CAT TCG
421/141                               451/151
GTC GAT GTC GTC TTC GCC GAC CCG CCC TAT AAT CTT CAG CTC GGC GGC ACG TTG CAC CGG
481/161                               511/171
CCC GAT CAG TCG CTG GTC GAT GCA GTG GAC GAC GAT TGG GAC CAG TTT GCT TCC TTC GAA
541/181                               571/191
GCC TAT GAC GCT TTC ACC CGC GCC TGG CTG CTT GCC TGC CGG CGT GTC CTG AAG CCC ACC
601/201                               631/211
GGC ACG CTC TGG GTC ATC GGT TCC TAC CAC AAT ATC TTC CGG GTC GGC GCG ATC CTC CAG
661/221                               691/231
GAC CTG CAC TTC TGG GTC TTG AAC GAT ATC ATC TGG CGC AAG ACC CAA CCC GAT GCC GAA
721/241                               751/251
CTT CAA GGG CGC CGC TTC CAG AAC GCG CAT GAA ACG CTG ATC TGG GCG ACG GCG AAC GCC
781/261                               811/271
AAG GCC AAG GGT TAT ACC TTC AAC TAC GAA GCG ATG AAG GCG GCG AAC GAC GAC GTT CAG
841/281                               871/291
ATG CGC TCC GAC TGG CTG TTC CCC ATC TGC TCC GGT TCC GAG CGG CTG AAG GGC GAC GAC
901/301                               931/311
GGC AAG AAA GTA CAC CCG ACG CAA AAG CCG GAA GCG CTG CTT GCC CGC ATC CTG ATG GCC
961/321                               991/331
TCG ACC AAG CCC GGG GAC GTC GTG CTT GAT CCG TTC TTC GGC TCC GGC ACC ACC GGG GCG
1021/341                              1051/351
GTC GCC AAG CGC CTC GGC CGG CAC TTC GTC GGG ATC GAG CGC GAG CAG GAC TAT ATC GAT
1081/361                              1111/371
GCC GCC GCC GAA CGT ATC GCG GCC GTG GAG CCG CTC GGC AAG GCC ACG CTC TCG GTC ATG
1141/381                              1171/391
ACC GGC AAG AAG GCG GAG CCG CGC GTC GCC TTC AAC ACT CTG GTG AAA GCG GGC TCA TC
1201/401                              1231/411
AAG CCC GGC ACG GTT CTG ACG GAT GCG AAG CGC CGC TAC AGC GCG ATC GTC CGC GCC GAC

FIGURE 1A. Rhizobium meliloti methytransferase gene sequence (continued)

1261/421                                1291/431
GGC ACG CTG GCG TCC GGC GGC GAG GCT GGA TCC ATT CAC CGC CTC GGC GCA AAA GTG CAG

1321/441                                1351/451
GGC CTC GAC GCC TGC AAC GGC TGG ACC TTC TGG CAC TTC GAG GAG GGA AGC GTA TTG AAA

1381/461                                1411/471
CCG ATC GAC GAG CTC AGA TCC GTC ATT CGA AAC GAC CTG GCA AAA CTG AAC TGA TCA ACC

1441/481                                1471/491
AGT TCC GCC TGG GTC TTC GAT AGG CGC CCC CTT CCG GTT TTT GTG CCT TCA GTC CCG GAT

1501/501                                1531/511
GAG CGC TTT AAA CGC CGG AAT CCG AAG AGG ATT CCG GGG CTT TGT ATC AAT GCG GGG CGT

1561/521                                1591/531
CAG CGT TAC AGC ATG GCA GCC GCT GCC AGG AGG GTG CCG CGT CCG AAG CTG GAT ACC GTA

1621/541                                1651/551
GCC GCG AGA TCG GCT TTC AGC CTT TCG GCG CCG GTG AAC TGA ACC GCG TGC AGC CG GCC

1681/561
GCT GCG CGC CTT CGA CAT

FIGURE 2. Rhizobium meliloti methytransferase peptide sequence

```
M S S V V S L A E I S R A A R P L N W L
D S I I K G D C V A A L N A L P D H S V
D V V F A D P P Y N L Q L G G T L H R P
D Q S L V D A V D D D W D Q F A S F E A
Y D A F T R A W L L A C R R V L K P T G
T L W V I G S Y H N I F R V G A I L Q D
L H P W V L N D I I W R K T Q P D A E L
Q G R R F Q N A H E T L I W A T A N A K
A K G Y T F N Y E A M K A A N D D V Q M
R S D W L F P I C S G S E R L X G D D G
K K V H P T Q K P E A L L A R I L M A S
T K P G D V V L D P F F G S G T T G A V
A K R L G R H F V G I E R E Q D Y I D A
A A E R I A A V E P L G K A T L S V M T
G K K A E P R V A F N T L V E S G L I K
P G T V L T D A K R R Y S A I V R A D G
T L A S G G E A G S I H R L G A K V Q G
L D A C N G W T F W H F E E G S V L K P
I D E L R S V I R N D L A K L N
```

FIGURE 3. Brucella abortus methytransferase gene sequence

DNA sequence 1731 b.p. AAAGGGTACGAA ... CATCGATGAAGA linear

1/1                                31/11
AAA GGG TAC GAA CAG CAC CCT CAA ATA TCG ATT ATG ACG CAA CTC CGC GAA ATT CAT TAT
61/21                              91/31
CAA ACT ACA CCC GAC AGG CAC TTC AGT CTG CGA GCG GCT GCC ACA CAC ACT GCA TCA TCG
121/41                             151/51
TCA TTT GCC GCC GGA TCA TAG ACC AAA AGA AAT AAC CAA GCC TTA TTG ATT GCG ACA TAT
181/61                             211/71
GCC GTT CCA GCC TTG CAC ATG GAT CAC GTC GTC ACG ATG ACA AGT CGA TAA TTA TCT CTG
241/81                             271/91
CCT TAT TGG GCG CGC AAA GGC CGC AAA GCC GGG CTT TCC CTG TGA TAT TAA GAA AAG ATT
301/101                            331/111
TAC GAT TTC AAG CAC TTG GCG TTA AGC GCA TAT TTA CCC TAC GCA GTA ACC ATA GGA ACA
361/121                            391/131
AGT TTT TTG CGT TCA CAG GTA ATC GAG TAT CCC ATG TCC CTA GTA CGT CTT GCG CAT GAG
421/141                            451/151
TTG CCC ATC GAG GCC CCG CGT ACC GCC TGG CTC GAC TCC ATC ATC AAA GGT GAT TGC GTT
481/161                            511/171
TCC GCG CTG GAG CGC CTG CCG GAT CAT TCC GTA GAC GTC ATC TTT GCC GAT CCG CCC TAT
541/181                            571/191
AAT CTC CAG CTT GGC GGC GAT CTG CAC CGT CCG GAT CAG TCC ATG GTC AGC GCC GTG GAC
601/201                            631/211
GAT CAT TGG GAC CAG TTT GAA AGC TTC CAG GCC TAT GAC GCC TTC ACC CGC GCC TGG CTG
661/221                            691/231
CTC GCC TGC CGC CGT GTG CTG AAG CCG AAT GGC ACC ATC TGG GTC ATC GGT TCC TAT CAC
721/241                            751/251
AAT ATT TTC CGC GTC GGC ACG CAG TTG CAG GAT CTG GGC TTC TGG CTC CTC AAC GAC ATT
781/261                            811/271
GTC TGG CGC AAG ACC AAT CCC ATG CCG AAT TTC CGT GGC CGC CGT TTC CAG AAT GCG CAT
841/281                            871/291
GAA ACG CTG ATC TGG GCT TCG CGT GAG CAG AAG GGC AAG GGA TAT ACT TTC AAT TAC GAG
901/301                            931/311
GCC ATG AAA GCG GCC AAT GAC GAT GTG CAG ATG CGT TCG GAC TGG CTG TTC CCG ATC TGC
961/321                            991/331
ACC GGC AGT GAA CGC CTG AAG GAC GAG AAC GGC GAC AAG GTC CAC CCG ACC CAG AAG CCG
1021/341                           1051/351
GAA GCA TTC TCG CGC GCG ATC ATG ATG GCT TCA AGC AAG CCG GGC GAC GTT ATT CTC GAC
1081/361                           1111/371
CCA TTC TTC GGT TCC GGC ACG ACC GGC GCG GTC GCC AAG CGG CTT GGC CGC CAT TTC GTC
1141/381                           1171/391
GGC ATC GAG CGT GAA CAG CCC TAT ATC GAC GCC GCA ACC GCC CGC ATC AAT GCC GTG GAG
1201/401                           1231/411
CCG CTT GGC AAG GCG AAC TCG ACG GTG ATG ACC GGC AAG CGC GCA GAG CCG CGC GTG GCC

FIGURE 3A. Brucella abortus methytransferase gene sequence (continued)

1261/421                         1291/431
TTC ACG AGC GTA ATG AAA GCG GGC CTT TTG CGT CCG GGA ACC GTG CTT TGT GAT GAA CGC

1321/441                         1351/451
CGC CGT TTT GCC GCC ATT GTT CGC GCC GAT GGG ACG CTG ACG GCC AAC GGC GAA GCC GGT

1381/461                         1411/471
TCA ATC CAT CGT ATT GGC GCC AGG GTT CAA GGG TTC GAT GCC TGC AAT GGC TGG ACC TTC

1441/481                         1471/491
TGG CAC TTT GAG GAA AAC GGC GTA CTG AAG CCT ATC GAT GCC CTG CGC AAG ATC ATC CGC

1501/501
GAA CAG ATG GCT GCG GCA GGT GCA TAA GAA AGT TTA ATA TCG GAC GAT CTC CAG TAA AGT

1561/521                         1591/531
CTG ATA GCA AGG CGC TCG AAG TTT TCA AAC TTC GGG CGC CTT CAT TCT TTC AGA AAG AAA

1621/541                         1651/551
GCT GTC GCG CCC GCA AAT CGT CGG CCA GTT TGG CTG CGC TGG TAA AAT GCA CCG CCT GCC

1681/561                         1711/571
AGC CCG CTT GCT TCG CAC CTT CCA CAT TGT GCA TCG TGT CAT CGA TGA AGA

FIGURE 4. Brucella abortus methytransferase peptide sequence

|                |         |
|----------------|---------|
| 421/141        | M S L V R L A H E |
|                | 451/151 |
| L P I E A P R T A W L D S I I K G D C V |         |
| 481/161        | 511/171 |
| S A L E R L P D H S V D V I F A D P P Y |         |
| 541/181        | 571/191 |
| N L Q L G G D L H R P D Q S M V S A V D |         |
| 601/201        | 631/211 |
| D H W D Q F E S F Q A Y D A F T R A W L |         |
| 661/221        | 691/231 |
| L A C R R V L K P N G T I W V I G S Y H |         |
| 721/241        | 751/251 |
| N I F R V G T Q L Q D L G F W L L N D I |         |
| 781/261        | 811/271 |
| V W R K T N P M P N F R G R R F Q N A H |         |
| 841/281        | 871/291 |
| E T L I W A S R E Q K G K G Y T F N Y E |         |
| 901/301        | 931/311 |
| A M K A A N D D V Q M R S D W L F P I C |         |
| 961/321        | 991/331 |
| T G S E R L K D E N G D K V H P T Q K P |         |
| 1021/341       | 1051/351 |
| E A L L A R I M M A S S K P G D V I L D |         |
| 1081/361       | 1111/371 |
| P F F G S G T T G A V A K R L G R H F V |         |
| 1141/361       | 1171/391 |

```
        M  S  L  V  R  L  A  H  E
421/141     451/151
L P I E A P R T A W L D S I I K G D C V
481/161            511/171
S A L E R L P D H S V D V I F A D P P Y
541/181            571/191
N L Q L G G D L H R P D Q S M V S A V D
601/201            631/211
D H W D Q F E S F Q A Y D A F T R A W L
661/221            691/231
L A C R R V L K P N G T I W V I G S Y H
721/241            751/251
N I F R V G T Q L Q D L G F W L L N D I
781/261            811/271
V W R K T N P M P N F R G R R F Q N A H
841/281            871/291
E T L I W A S R E Q K G K G Y T F N Y E
901/301            931/311
A M K A A N D D V Q M R S D W L F P I C
961/321            991/331
T G S E R L K D E N G D K V H P T Q K P
1021/341           1051/351
E A L L A R I M M A S S K P G D V I L D
1081/361           1111/371
P F F G S G T T G A V A K R L G R H F V
1141/361           1171/391
G I E R E Q P Y I D A A T A R I N A V E
1201/401           1231/411
P L G K A E L T V M T G K R A E P R V A
1261/421           1291/431
F T S V M E A G L L R P G T V L C D E R
1321/441           1351/451
R R F A A I V R A D G T L T A N G E A G
1381/461           1411/471
S I H R I G A R V Q G F D A C N G W T F
1441/481           1471/491
W H F E E N G V L K P I D A L R K I I R
1501/501
E Q M A A A G A
```

FIGURE 5. Agrobacterium tumefaciens methytransferase gene sequence

DNA sequence   255 b.p.   ATTTTCGCCGAT ... TGGATCCTCAAC linear

1/1                                          31/11
ATT TTC GCC GAT CCG CCG TAT AAT CTC CAG CTT GGC GGC AAC GTG CAC CGG CCC GAT CAG

61/21                                        91/31
TCG CTG GTC GAT GCC GTT GAT GAC GAA TGG GAC CAG TTC GCC TCC TTC GAC GCC TAT GAC

121/41                                       151/51
GCC TTC ACC CGC GCC TGG CTG CTC GCC TGC CGC CGT GTG CTG AAA CCG AAC GGC ACC ATC

181/61                                       211/71
TGG GTC ATC GGC TCC TAT CAC AAT ATC TTC CGC GTC GGC GCC ATG CTC CAG AAC CTC GAT

241/81
TTC TGG ATC CTC AAC

FIGURE 6. <u>Agrobacterium tumefaciens</u> methytransferase peptide sequence

Sequence of *Helicobacter pylori* CcrM homolog and putative restriction endonuclease. Boxes around 'ATG' indicate start codons. Circled nucleotides ('TAA') indicate a stop codon. The start codon of the downstream open reading frame overlaps the stop codon of the gene encoding the CcrM homolog.

```
1                                     31
AAC GGG CAT GCT TTG CGA TTT GCA TTT GAA CGG ATC GGG GAG TTA TGC GTT TTT GTT GTA
61                                    91
TCG TTT AAA ATA GGT GGG GAT AGG TAG CTT CTA TCA TTT GAT GCA TTT GAT GAG AAC AAA
121                                   151
GCT AGG GAC TAA ACA TTA AGA TAG CCT TAA AAC GCT TGT GTT AAA ATG GCC AGA GTA GCA
181                                   211
GAT ATA AAA GGC TAG TTA ATC ATG GAT TTT TTA AAA GAA AAC TTA AAC ACT ATC ATA GAG
241                                   271
GGG GAT TGT TTA GAA AAA TTG AAA GAT TTT CCT AAT AAA AGC GTT GAT TTT ATC TTT GCT
301                                   331
GAC CCC CCA TAT TTT ATG CAA ACA GAG GGA GAA TTG AAG CGT TTT GAA GGC ACA AAA TTT
361                                   391
CAA GGC GTT GAG GAT CAT TGG GAT AAA TTT GGC TCT TTT GAA GAA TAC GAT ACC TTT TGT
421                                   451
TTG GGT TGG TTA AAA GAA TGC CAA AGG ATT TTA AAA GAT AAT GGC AGT ATT TGT GTG ATA
481                                   511
GGG AGT TTT CAA AAT ATT TTT AGA ATT GGT TTT CAT TTG CAA AAT TTA GGG TTT TGG ATA
541                                   571
CTC AAT GAT ATT GTT TGG TAC AAG AGC AAT CCG GTG CCT AAT TTT GCT GGC AAG AGA CTA
601                                   631
TGC AAC GCC CAT GAA ACG CTT ATT TGG TGC GCT AAA CAC AAA AAC AAC AAA GTT ACC TTT
661                                   691
AAT TAT AAA ACA ATG AAG TAC CTC AAT AAC AAT AAA CAA GAA AAA TCG GTT TGG CAA ATC
721                                   751
CCT ATT TGC ATG GGT AAC GAA AGG CTA AAA GAC GCG CAA GGT AAA AAA GTG CAT TCC ACG
781                                   811
CAA AAA CCA GAA GCG CTC TTA AAA AAA ATC ATT TTA AGC GCG ACT AAA CCT AAA GAC ATT
841                                   871
ATT TTA GAT CCC TTT TTT GGC ACA GGC ACA ACA GGG GCT GTG GCT AAA TCC ATG AAC AGG
901                                   931
TAT TTT ATT GGC ATT GAA AAA GAT TCT TTT TAT ATC AAA GAA GCG GCA AAA CGC CTT AAT
961                                   991
AGC ACT AGG GAT AAA AGC GAT TTT ATC ACT AAT TTA GAT TTA GAA ACT AAA CCC CCA AAA
```

FIGURE 7A. (Continued)

```
1021                          1051
ATC CCT ATG AGT CTT TTA ATT TCT AAA CAA TTA CTC AAA ATT GGA GAT TTT TTA TAC TCA
1081                          1111
TCT AAC AAA GAA AAA ATT TGT CAA GTT TTA GAA AAC GGA CAA GTG AGG GAT AAT GAA AAC
1141                          1171
TAT GAA ACT TCT ATT CAT AAG ATG AGC GCT AAA TAT TTG AAT AAA ACT AAC CAT AAT GGC
1201                          1231
TGG AAA TTT TTT TAT GCG TAT TAC CAA AAT CAA TTT TTA TTG TTA GAT GAA TTG CGT TAT
1261                          1291
ATC TGC CAA AGG GAC TCT AAA TGG ACT ATC AAA CCT TTA ACG AGA TTT TTA ATC GTT TTG
1321                          1351
TTT TTG GAA CAT CTA AAG CAA AAT TAC TTG AAA ATA TTG CCG AAA ATC CTG AAC GCT ATT
1381                          1411
TGG GGA TTT TTA GAC CCA CTA AGC CTA AGA CAA AAC TAT TAC AAA ATT TAT TGA CTT CTC
1441                          1471
ATG AGA TTA AGT TTG GCG ATG CGT TTG AAT GCT TAA TAG AAC AAT ATT AAA AGC ATA
1501                          1531
ACT TTT CAC CTT TAT CTA AAA AAA TTC CTT ATT ACA ATA AGG ATA AAG AAA AAA GGG AAT
1561                          1591
CTT TAG AAT TAG ATC AGT TTG CTA AAA AAG ATA ACA CAT ATT ATT TTA TAG AAC AAA AAA
1621                          1651
TGC GAG ATG ACC ATG ACA GCA CCA AAA AGA GAG GGC AAA TAG ATA ACT TTG AAA GGA AAT
1681                          1711
TAG AGG CTT TAG TCC ATC GTT ATG GCG AAA ACA TTC AAG GCT ATT TTT ATT TTA TAG ATG
1741                          1771
AGG GTT TGA ATA AAA ATC AAA ATT ACT ATA AAG AAG AAT TGC AAA AAT TAT CTG TTG ATT
1801                          1831
ATG GCG TGC CTT TGA GTT TGT GTT ATG GTA AGG GGT TGT TTG AAT CTC TTA ATA TCC CGC
1861                          1891
AAG TTT GGG ATG AGG TTT TAA GCC ATT TAG TGC GAT GGC GTG AAA CCT TAC CCG ATT TAC
1921                          1951
CCA GTT TGA ATT TTG ATG AAA ATC CTT TAG AAA GTT TTA GAG AAA TCA AAG ATT TAG CGC
1981                          2011
CAA GCG TTT ATA GGA AGC TTT TGG ATA ATG ATG AAA TTT TCA ATC TTG TGT TAA TTT TAT
2041                          2071
TCC CAG AAC AAA AAG TTT TAA AAA TGT TAG TAG AGC ATT TTA GAC AAC AAA AT (incomplete)
```

FIGURE 8. Amino acid sequence of *Helicobacter pylori* CcrM homolog
The numbers above the amino acid sequence indicate:
Nucleotide number in the accompanying DNA sequence/amino acid number in the protein.
Hence, each line contains 20 amino acids corresponding to 60 nucleotides. The asterisk
Denotes the position of the stop codon.

```
202/1                          232/11
M D F L K E N L N T I I E G D C L E K L

262/21                         292/31
K D F P N K S V D F I F A D P P Y F M Q

322/41                         352/51
T E G E L K R F E G T K F Q G V E D H W

382/61                         412/71
D K F G S F E E Y D T F C L G W L K E C

442/81                         472/91
Q R I L K D N G S I C V I G S F Q N I F

502/101                        532/111
R I G F H L Q N L G F W I L N D I V W Y

562/121                        592/131
K S N P V P N F A G K R L C N A H E T L

622/141                        652/151
I W C A K H K N N K V T F N Y K T M K Y

682/161                        712/171
L N N N K Q E K S V W Q I P I C M G N E

742/181                        772/191
R L K D A Q G K K V H S T Q K P E A L L

802/201                        832/211
K K I I L S A T K P K D I I L D P F F G

862/221                        892/231
T G T T G A V A K S M N R Y F I G I E K

922/241                        952/251
D S F Y I K E A A K R L N S T R D K S D

982/261                        1012/271
F I T N L D L E T K P P K I P M S L L I

1042/281                       1072/291
S K Q L L K I G D F L Y S S N K E K I C

1102/301                       1132/311
Q V L E N G Q V R D N E N Y E T S I H K

1162/321                       1192/331
M S A K Y L N K T N H G W K F F Y A Y

1222/341                       1252/351
Y Q N Q F L L L D E L R Y I C Q R D S *
```

DNA ADENINE METHYLTRANSFERASES AND USES THEREOF

CROSS REFERENCES TO RELATED APPLICATIONS

The present application claims priority from U.S. provisional Application No. 60/020,089, filed Sep. 19, 1996.

GOVERNMENT RIGHTS

The research that led to this application was supported in part by an NIH grant, and the government may have certain rights to the invention.

BACKGROUND OF THE INVENTION

A. Field of the Invention

This invention pertains to the field of microbiology and to the treatment of conditions caused by microbes. In particular, this invention pertains to the isolation, sequencing, and detection of a DNA adenine methyltransferase gene from a variety of micro-organisms.

B. Related Art

Most organisms modify their genomic DNA by the methylation of specific nucleotide bases. DNA methylation is critical to gene regulation and repair of mutational lesions (for recent reviews see Jost and Saluz, *DNA Methylation, Molecular Biology and Biological Significance.* Birhauser Verlag, Basel, Switzerland (1993); Palmer and Marinus, *Gene* 143:1–12 (1994)).

DNA methylation is catalyzed by a class of enzymes of varying substrate specificity called DNA methyltransferase enzymes. A DNA methyltransferase from the bacterium *Caulobacter crescentus,* cell cycle regulated methyltransferase ("CcrM" refers to the protein and "ccrM" denotes the gene), methylates the adenine residue in the recognition sequence GANTC (Zweiger et al., *J. Mol. Biol.* 235: 472–485, 1994; N denotes any nucleotide). CcrM is unusual, as it is not part of a restriction modification system, and is the only known prokaryotic DNA methyltransferase shown to be essential for viability (Stephens et al., *Proc. Natl. Acad. Sci.* 93:1210–1214, 1996) outside of a restriction modification system (i.e., a coexpressed methylase and restriction enzyme which recognize a same nucleotide sequence).

The CcrM protein, and therefore its DNA methylation activity, is present only at the predivisional stage of the cell cycle (Zweiger et al., *J. Mol. Biol.* 235: 472–485, 1994; Stephens et al., *Proc. Natl. Acad. Sci.* 93:1210–1214, 1996). This is controlled in two ways; the ccrM gene is transcribed only in the predivisional cell (Stephens et al., *J. Bacteriol.* 177:1662–1669, 1995) and the CcrM protein is highly unstable and is completely degraded by the time of cell division in a Lon protease dependent process (Wright et al., *Genes and Development* 10:1532–1542, 1996).

SUMMARY OF THE INVENTION

The present invention comprises the isolation and sequence of a number of methyltransferase-encoding nucleic acids and their gene products, including the methyltransferase gene from *Rhizobium meliloti, Brucella abortus, Agrobacterium tumefaciens,* and *Helicobacter pylori.* These novel DNA methyltransferases are potential targets for new antimicrobial agents. Under the assay conditions provided herein, these enzymes exhibit a novel property called processivity.

In one series of embodiments, the invention comprises an isolated nucleic acid that encodes a *Rhizobium meliloti* DNA methyltransferase, including a nucleic acid having SEQ ID NO:1; cells that contain and express such nucleic acids; and isolated DNA adenine methyltransferases encoded by such a nucleic acid (e.g., SEQ ID NO: 2).

In another series of embodiments, the invention comprises an isolated nucleic acid that encodes a *Brucella abortus* DNA methyltransferase (e.g., SEQ ID NO:4), particularly a nucleic acid having SEQ ID NO:3; cells that contain and express such nucleic acids, and isolated DNA adenine methyltransferases encoded by such nucleic acid.

In another series of embodiments, the invention comprises an isolated nucleic acid (e.g., SEQ ID NO: 5) that encodes a partial sequence of *Agrobacterium tumefaciens* DNA methyltransferase (e.g., SEQ ID NO: 6).

In another series of embodiments, the invention comprises an isolated nucleic acid (e.g., SEQ ID NO: 7) that encodes a *Helicobacter pylori* DNA methyltransferase (e.g., SEQ ID NO: 8); cells that contain and express such nucleic acids, and isolated DNA adenine methyltransferases encoded by such nucleic acid.

The ccrM genes for *Rhizobium meliloti, Agrobacterium tumefaciens* and *Brucella abortus* exhibit homology to Caulobacter ccrM. It is highly likely that the ccrM homologs are a new DNA methyltransferase family which is not part of a restriction modification system.

Both Caulobacter and Rhizobium ccrM are essential for viability. Neither gene can be disrupted from the chromosome unless a copy is provided in trans on a plasmid (Stephens et al., *Proc. Nat'l. Acad. Sci.* 93:1210–1214, 1996; this application). The overexpression of both Rhizobium and Caulobacter ccrM results in defects in cell morphology and cell division, demonstrating the importance of DNA methylation in these two bacteria. Hemimethylated DNA could be detected in both Rhizobium and Caulobacter. In the case of Caulobacter this is due to the cell cycle regulation of ccrM.

In another embodiment, this invention provides for vectors incorporating any of the above-described nucleic acids. The vectors preferably include the above-described nucleic acid operably linked to (under the control of) a promoter, either constitutive or inducible. The vector can also include an initiation and a termination codon.

In another embodiment, this invention provides for cells that contain the above-mentioned nucleic acids and cells that express the above-mentioned nucleic acids that encode adenine methyltransferases. For example, host cells may be transfected with a nucleic acid of SEQ ID NO: 1, 3, 5, or 7.

In addition to providing for host cells stably transfested with nucleic acids encoding adenine methyltransferases, this invention also uses these transfected host cells to detect compounds that are capable of inhibiting adenine methyltransferase.

The invention further provides for nucleic acid probes that are capable of selectively hybridizing to a nucleic acid encoding an adenine methyltransferase. For example, the nucleic acid probe can be the nucleic acid of SEQ ID NO: 1, 3, 5, or 7. These probes can be used to measure or detect nucleic acids encoding adenine methyltransferases. The probes are incubated with a biological sample to form a hybrid of the probe with complementary nucleic acid sequences present in the sample. The extent of hybridization of the probe to these complementary nucleic acid sequences is then determined.

In another embodiment, this invention provides for antibodies to the methyltransferases encoded by the above-mentioned nucleic acids. Particularly preferred antibodies specifically bind a polypeptide comprising at least 10, more preferably at least 20, 40, 50, and most preferably at least 100, 200, and even 300 contiguous amino acids, or even the full length polypeptide encoded by a nucleic acid selected from the group consisting of SEQ ID NO: 1, SEQ ID NO: 3, SEQ ID NO: 5, or SEQ ID NO: 7; wherein said polypeptide elicits the production of an antiserum or antibody which specifically binds to a polypeptide selected from the group consisting of SEQ ID NO: 2, SEQ ID NO: 4, SEQ. ID NO: 6, or SEQ ID NO: 8, wherein the antiserum or antibody preferably does not cross-react with the *C. crescentus* adenine methyltransferase. The antibody can be polyclonal or monoclonal. The antibody can also be humanized or human.

This invention also provides for cells (e.g., recombinant cells such as hybridomas or triomas) which synthesize any of the above-described antibodies.

This invention also provides for kits for the detection and/or quantification of the above-mentioned nucleic acids. The kit can include a container containing one or more of any of the above identified nucleic acids, amplification primers, and antibodies with or without labels, free, or bound to a solid support as described herein. The kits can also include instructions for the use of one or more of these reagents in any of the assays described herein.

This invention further provides for methods and assays for identification and screening for novel antibiotics that target the methyltransferases of this invention. Such assays include those for screening for inhibitors of DNA methyltransferase activity that comprises: i. contacting in an aqueous reaction mixture a nucleic acid encoding a DNA methyltransferase wherein said methyltransferase has a molecular weight of about 30–45 kilodaltons and binds to a polyclonal antibody that specifically binds to a polypeptide from the group of polypeptides having SEQ ID NO:2, SEQ ID NO:4, SEQ ID NO:6, and SEQ ID NO:8 with an antisense agent that inhibits the expression of the methyltransferase; and ii. detecting the level of inhibition relative to a control reaction mixture that is substantially identical to the reaction mixture of step i except that the antisense agent is not present in an amount effective to inhibit the expression of the methyltransferase. The methods include both in vivo and in vitro methods. The antisense agents can either be added exogenously or are produced endogenously through conventional recombinant gene methods.

Other methods for screening include methods for assaying for inhibitors of DNA methyltransferase activity comprising the steps of: i. contacting an aqueous reaction mixture containing a DNA methyltransferase wherein said methyltransferase has a molecular weight of about 30–45 kilodaltons and binds to a polyclonal antibody that specifically binds to a polypeptide from the group of polypeptides having SEQ ID NO:2, SEQ ID NO:4, SEQ ID NO:6, and SEQ ID NO:8 with an agent that inhibits the biological activity of the methyltransferase; and, ii. detecting the level of inhibition relative to a control reaction mixture that is substantially identical to the reaction mixture of step i except that the inhibitory agent is not present in an amount effective to inhibit the expression of the methyltransferase. The DNA methyltransferase is not contained within a living cell or the assay can be an in vivo assay where the enzyme is inhibited within a living cell.

Processive assays are also described herein such as an assay for detecting antibiotics that target processive adenine methyltransferases, comprising: i) contacting a methyltransferase with a methyltransferase substrate in the presence and absence of a test substance; and b) detecting the enzymatic activity of the methyltransferase in the presence and absence of the test substance.

Finally, this invention also provides therapeutic methods. These include methods of detecting infections with Brucella spp. and *H. pylori* by detecting the presence or absence of specific sequences of Brucella or *H. pylori* adenine methyltransferases or by detecting the proteins themselves using antibodies. Other methods include treating conditions caused by Agrobacterium spp., Rhizobium spp, and Helicobacter spp. Other methods involve administering to a mammal a therapeutically effective dose of a composition comprising a methyl transferase inhibitor and a pharmacological excipient. For animal associated bacteria, methods are preferably performed on mammals such as mice, rats, rabbits, sheep, goats, pigs, more preferably on primates including human patients. Of course for plant associated bacteria such as Agrobacterium and Rhizobium spp., the preferred methods are performed on their respective host plants.

BRIEF DESCRIPTION OF THE SEQUENCES

FIG. 1 is a sequence of a nucleic acid that encodes a *Rhizobium meliloti* DNA methyltransferase (SEQ ID NO:1). The start codon is boxed and the stop codon is circled.

FIG. 2 is the peptide sequence of a *Rhizobium meliloti* DNA methyltransferase (SEQ ID NO:2).

FIG. 3 is a sequence of a nucleic acid that encodes a *Brucella abortus* DNA methyltransferase (SEQ ID NO:3). The start codon is boxed and the stop codon is circled.

FIG. 4 is a peptide sequence of a *Brucella abortus* DNA methyltransferase (SEQ ID NO:4).

FIG. 5 is a partial sequence of a nucleic acid that encodes an *Agrobacterium tumefaciens* DNA methyltransferase (SEQ ID NO:5).

FIG. 6 is a partial peptide sequence of an *Agrobacterium tumefaciens* DNA methyltransferase (SEQ ID NO:6).

FIG. 7 is a complete sequence of a nucleic acid that encodes a *Helicobacter pylori* DNA methyltransferase (SEQ ID NO:7).

FIG. 8 is a complete peptide sequence of a *Helicobacter pylori* DNA methyltransferase (SEQ ID NO:8).

LIST OF TABLES

Table 1 is a comparison of the sequences of *Caulobacter crescentus* ("Ccr"), *Rhizobium meliloti* ("Rme"), *Agrobacterium tumefaciens* ("Atu"), *Brucella abortus* ("Bab"), and *Helicobacter pylori* ("Hpy") DNA adenine methyltransferases.

DETAILED DESCRIPTION OF THE INVENTION

A. Definitions

The term "biological activity" in the context of DNA methyltransferase refers to the capacity of the enzyme to act as a methyltransferase as defined herein.

The term "methyltransferase" denotes an enzyme that transfers a methyl group from a methyl donor to a specific site on a nucleic acid substrate, wherein the specific site is preferably a specific base in a characteristic sequence present in the nucleic acid substrate.

The term "processive" methyltransferase signifies that, under the assay conditions used, whenever there is more than one potential methylation site on a DNA substrate, after methylating a first site the methyltransferase methylates the second or subsequent sites without dissociating from the DNA substrate.

The term "DNA-dependent" signifies that the methyltransferase tends to lose activity in solution in the absence of a DNA substrate.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); and Cassol et al., 1992; Rossolini et al., *Mol. Cell. Probes* 8:91–98 (1994)). The term nucleic acid is used interchangeably with gene, cDNA, and mRNA encoded by a gene.

The phrase "exogenous" or "heterologous nucleic acid" generally denotes a nucleic acid that has been isolated, cloned and ligated to a nucleic acid with which it is not combined in nature, and/or introduced into and/or expressed in a cell or cellular environment other than the cell or cellular environment in which said nucleic acid or protein may typically be found in nature. The term encompasses both nucleic acids originally obtained from a different organism or cell type than the cell type in which it is expressed, and also nucleic acids that are obtained from the same cell line as the cell line in which it is expressed.

"Nucleic acid probes" may be DNA or RNA fragments. DNA fragments can be prepared, for example, by digesting plasmid DNA, or by use of PCR, or synthesized by either the phosphoramidite method described by Beaucage and Carruthers, *Tetrahedron Lett.* 22:1859–1862 (1981), or by the triester method according to Matteucci, et al., *J. Am. Chem. Soc.,* 103:3185 (1981), both incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid.

The phrase "selectively hybridizing to" refers to a nucleic acid probe that hybridizes, duplexes or binds only to a particular target DNA or RNA sequence when the target sequences are present in a preparation of total cellular DNA or RNA. "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., *Molecular Cloning: A Laboratory Manual* (2nd ed.), Vols. 1–3, Cold Spring Harbor Laboratory (1989), or *Current Protocols in Molecular Biology,* F. Ausubel et al., ed. Greene Publishing and Wiley-Interscience, New York (1987).

The phrase "a nucleic acid sequence encoding" refers to a nucleic acid which contains sequence information for a structural RNA such as rRNA, a tRNA, or the primary amino acid sequence of a specific protein or peptide, or a binding site for a trans-acting regulatory agent. This phrase specifically encompasses degenerate codons (i.e., different codons which encode a single amino acid) of the native sequence or sequences which may be introduced to conform with codon preference in a specific host cell.

"Nucleic acid probes" may be DNA or RNA fragments. DNA fragments can be prepared, for example, by digesting plasmid DNA, or by use of PCR, or synthesized by either the phosphoramidite method described by Beaucage and Carruthers, *Tetrahedron Lett.* 22:1859–1862 (1981), or by the triester method according to Matteucci, et al., *J. Am. Chem. Soc.,* 103:3185 (1981), both incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid.

The phrase "selectively hybridizing to" refers to a nucleic acid probe that hybridizes, duplexes or binds only to a particular target DNA or RNA sequence when the target sequences are present in a preparation of total cellular DNA or RNA. "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., *Molecular Cloning: A Laboratory Manual* (2nd ed.), Vols. 1–3, Cold Spring Harbor Laboratory (1989), or *Current Protocols in Molecular Biology,* F. Ausubel et al., ed. Greene Publishing and Wiley-Interscience, New York (1987).

The term "isolated", when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated DNA methyltransferase gene is separated from open reading frames which naturally flank the gene and encode a protein other than methyltransferase. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "recombinant" or "engineered" when used with reference to a nucleic acid or a protein generally denotes that the composition or primary sequence of said nucleic acid or protein has been altered from the naturally occurring sequence using experimental manipulations well known to those skilled in the art. It may also denote that a nucleic acid or protein has been isolated and cloned into a vector or a nucleic acid that has been introduced into or expressed in a cell or cellular environment, particularly in a cell or cellular environment other than the cell or cellular environment in which said nucleic acid or protein may be found in nature.

The term "recombinant" or "engineered" when used with reference to a cell indicates that the cell replicates or expresses a nucleic acid, or produces a peptide or protein encoded by a nucleic acid, whose origin is exogenous to the cell. Recombinant cells can express nucleic acids that are not found within the native (nonrecombinant) form of the cell. Recombinant cells can also express nucleic acids found in the native form of the cell wherein the nucleic acids are reintroduced into the cell by artificial means.

The following terms are used to describe the sequence relationships between two or more nucleic acids or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as the nucleic acid sequence of SEQ ID NO: 1, 3, 5, or 7, or may comprise a complete cDNA or gene sequence.

Optimal alignment of sequences for aligning a comparison window may be conducted by the local homology algorithm of Smith and Waterman (1981) Adv. Appl. Math. 2:482, by the homology alignment algorithm of Needleman and Wunsch (1970) J. Mol. Biol. 48:443, by the search for similarity method of Pearson and Lipman (1988) Proc. Natl. Acad. Sci. (USA) 85:2444, or by computerized implementations of these algorithms (GAP, BESTFIT, FASTA, and TFASTA in the Wisconsin Genetics Software Package Release 7.0, Genetics Computer Group, 575 Science Dr., Madison, Wis.).

The terms "substantial identity" or "substantial sequence identity", as applied to nucleic acid sequences and as used herein, denote a characteristic of a polynucleotide sequence, wherein the polynucleotide comprises a sequence that has at least 85 percent sequence identity, preferably at least 90 to 95 percent sequence identity, and more preferably at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

As applied to polypeptides, the terms "substantial identity" or "substantial sequence identity" mean that two peptide sequences, when optimally aligned, such as by the programs GAP or BESTFIT using default gap weights, share at least 70 percent sequence identity, preferably at least 80 percent sequence identity, more preferably at least 90 percent sequence identity, and most preferably at least 95 percent amino acid identity or more. "Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

The term "substantially identical" in the context of two reaction mixtures refers to reaction mixtures that are considered by those of skill to be sufficiently similar that scientifically valid comparisons can be made between them so as to compare relative activity due to the presence or absence of an inhibitor molecule.

A cell has been "transformed" by an exogenous nucleic acid when such exogenous nucleic acid has been introduced inside the cell membrane. Exogenous DNA may or may not be integrated (covalently linked) into chromosomal DNA making up the genome of the cell. The exogenous DNA may be maintained on an episomal element, such as a plasmid. A stably transformed or transfected eukaryotic cell is generally one in which the exogenous DNA has become integrated into the chromosome so that it is inherited by daughter cells through chromosome replication, or one which includes stably maintained extrachromosomal plasmids. This stability is demonstrated by the ability of the eukaryotic cell to establish cell lines or clones comprised of a population of daughter cells containing the exogenous DNA.

"Adenine methyltransferase substrate" refers to a nucleic acid that is acted upon by a DNA methyltransferase to undergo a methylation at an adenine residue. The optimum substrate contains at least one GANTC site and is preferably of a length that promotes ease of manipulation and yields easily resolvable methylation and/or restriction products, preferably a 45 base pair or longer oligonucleotide or plasmid.

The phrase "an essential adenine DNA methyltransferase" indicates that, in the absence of this enzyme activity at the appropriate stage in the cell cycle, organisms that normally express adenine DNA methyltransferase at that stage will die. Enzyme activity may be impaired by a mutation in the enzyme, by the use of antisense nucleic acid, by intracellular proteolysis of the enzyme, or by the administration of an inhibitor of the enzyme.

"Restriction" denotes the action of hydrolyzing a single or double stranded nucleic acid at a specific sequence or site. "Restriction enzyme" is a nuclease that recognizes a specific sequence or site of a nucleic acid, and cleaves the nucleic acid at that site. "Restriction site" is the particular sequence or site recognized and hydrolyzed by a restriction enzyme.

The phrase "specifically binds to an antibody" or "specifically immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised to adenine methyltransferase with the amino acid sequence depicted in SEQ ID NO: 2, 4, 6, or 8 can be selected to obtain antibodies specifically immunoreactive with that adenine methyltransferase and not with other proteins. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) Antibodies, *A Laboratory Manual,* Cold Spring Harbor Publications, New York, for a description of immunoassay formats and conditions that can be used to determine specific immunoreactivity.

B. General Background

This invention relates to isolated nucleic acid sequences encoding DNA adenine methyltransferases. DNA methyltransferases are present in gram-negative bacteria such as the free living bacteria Caulobacter, the agriculturally important nitrogen-fixing bacterium Rhizobium and the highly infectious animal pathogen Brucella. The precise sequences and properties of these methyltransferase genes and enzymes are unknown. Prior to the work summarized herein, it was not clear whether the methyltransferases of other organisms would have homologous sequences and properties.

The procedure for obtaining methyltransferase genes from selected organisms generally involves constructing or obtaining gene libraries from selected organisms, detecting and isolating the desired gene, cloning it, and expressing it in a suitable bacterial strain or transformed cell line.

The nucleic acid compositions of this invention, whether RNA, cDNA, genomic DNA, or a hybrid of the various combinations, may be isolated from natural sources or may be synthesized in vitro. The nucleic acids claimed may be present in transformed or transfected whole cells, in a transformed or transfected cell lysate, or in a partially purified or substantially pure form.

Techniques for nucleic acid manipulation of genes encoding the DNA adenine methyltransferases such as generating libraries, subcloning into expression vectors, labeling probes, DNA hybridization, and the like are described generally in Sambrook, et al., *Molecular Cloning-A Laboratory Manual* (2nd Ed.), Vol. 1–3, Cold Spring Harbor Laboratory, Cold Spring Harbor, N.Y., 1989, which is incorporated herein by reference. This manual is hereinafter referred to as "Sambrook, et al."

Nucleic acids and proteins are detected and quantified herein by any of a number of means known to those of skill in the art. These include analytical biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like. The detection of nucleic acids proceeds by well known methods such as Southern analysis, northern analysis, gel electrophoresis, PCR, radiolabeling, scintillation counting, and affinity chromatography.

1. Isolation of Nucleic Acids Encoding DNA Adenine Methyltransferases

There are various methods of isolating the DNA sequences encoding DNA adenine methyltransferases. For example, DNA is isolated from a genomic or cDNA library using labelled oligonucleotide probes (e.g., probes having sequences complementary to the sequences disclosed herein, such as SEQ ID NO: 1, 3, 5, 7, 9–11). The libraries are generated from DNA and mRNA from cultures of bacteria that are generated from stock cultures. Stock cultures are commercially available from a variety of sources including international depositories such as the American Type Culture Collection.

The probes for surveying the libraries can be used directly in hybridization assays to isolate DNA encoding DNA adenine methyltransferases. Alternatively, probes can be designed for use in amplification techniques such as PCR, and DNA encoding DNA adenine methyltransferases may be isolated by using methods such as PCR (see below).

Methods for making and screening DNA libraries are well established. See Gubler, U. and Hoffman, B. J. *Gene* 25:263–269, 1983 and Sambrook, et al. To prepare a genomic library, the DNA is generally extracted from cells and either mechanically sheared or enzymatically digested to yield fragments of about 12–20 kb. The fragments are then separated by gradient centrifugation from undesired sizes and are subcloned in bacteriophage lambda vectors. These vectors and phage are packaged in vitro, as described in Sambrook, et al. The vector is transformed into a recombinant host for propagation, screening and cloning. Recombinant phage are analyzed by plaque hybridization as described in Benton and Davis, *Science,* 196:180–182 (1977). Colony hybridization is carried out as generally described in M. Grunstein et al. *Proc. Natl. Acad. Sci.* USA., 72:3961–3965 (1975).

DNA encoding a DNA adenine methyltransferase is identified in either cDNA or genomic libraries by its ability to hybridize with nucleic acid probes, for example on Southern blots, and these DNA regions are isolated by standard methods familiar to those of skill in the art. See Sambrook, et al. The nucleic acid sequences of the invention are typically identical to or show substantial sequence identity (determined as described below) to the nucleic acid sequence of SEQ ID. No. 1, 3, 5, or 7. Nucleic acids encoding DNA adenine methyltransferases will typically hybridize to the nucleic acid sequence of SEQ ID NO: 1, 3, 5, or 7 under stringent conditions. For example, nucleic acids encoding DNA adenine methyltransferases will hybridize to the nucleic acid of sequence ID No. 1 under the hybridization and wash conditions of 50% formamide at 42° C. Other stringent hybridization conditions may also be selected. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents and the extent of base mismatching, the combination of parameters is more important than the absolute measure of any one.

Various methods of amplifying target sequences, such as the polymerase chain reaction, can also be used to prepare DNA encoding DNA adenine methyltransferase. Polymerase chain reaction (PCR) technology is used to amplify such nucleic acid sequences. The isolated sequences encoding DNA adenine methyltransferase may also be used as templates for PCR amplification.

In PCR techniques, oligonucleotide primers complementary to the two 3' borders of the DNA region to be amplified are synthesized. The polymerase chain reaction is then carried out using the two primers. See *PCR Protocols: A Guide to Methods and Applications.* (Innis, M, Gelfand, D., Sninsky, J. and White, T., eds.), Academic Press, San Diego (1990). Primers can be selected to amplify the entire regions encoding a full-length DNA adenine methyltransferase or to amplify smaller DNA segments as desired.

PCR can be used in a variety of protocols to isolate nucleic acids encoding the DNA adenine methyltransferases. In these protocols, appropriate primers and probes for amplifying DNA encoding DNA adenine methyltransferases are generated from analysis of the DNA sequences listed herein. For example, the oligonucleotides of SEQ ID Nos. 9–11 can be used in a PCR protocol as described in example 1 herein to amplify regions of DNA's encoding methyl transferase proteins. Once such regions are PCR-amplified, they can be sequenced and oligonucleotide probes can be prepared from sequence obtained. These probes can then be used to isolate DNA's encoding DNA adenine methyltransferases, similar to the procedure used in examples 1–4 herein. DNA adenine methyltransferases can be isolated from a variety of different cellular sources using this procedure. Other oligonucleotide probes in addition to those of SEQ ID NO: 1, 3, 5, 7 can also be used in PCR protocols to isolate cDNAs encoding the DNA adenine methyltransferases. Such probes are subsequences of the full-length coding sequences and can be from 20 bases to full length and preferably 30–50 bases in length.

Oligonucleotides for use as probes are chemically synthesized according to the solid phase phosphoramidite triester method first described by Beaucage, S. L. and Carruthers, M. H., 1981, *Tetrahedron Lett.*, 22(20) :1859–1862 using an automated synthesizer, as described in Needham-VanDevanter, D. R., et al., 1984, *Nucleic Acids Res.*, 12:6159–6168. Purification of oligonucieotides is by either native acrylamide gel electrophoresis or by anion-exchange HPLC as described in Pearson, J. D. and Regnier, F. E., 1983, *J. Chrom.*, 255:137–149. The sequence of the synthetic oligonucleotide can be verified using the chemical degradation method of Maxam, A. M. and Gilbert, W. 1980, in Grossman, L. and Moldave, D., eds. Academic Press, New York, *Methods in Enzymology*, 65:499–560.

Other methods known to those of skill in the art may also be used to isolate DNA encoding the DNA adenine methyltransferase. See Sambrook, et al. for a description of other techniques for the isolation of DNA encoding specific protein molecules.

2. Expression of Methyltransferase

Once DNA encoding DNA adenine methyltransferases is isolated and cloned, one can express the DNA adenine methyltransferases in a variety of recombinantly engineered cells to ascertain that the isolated gene indeed encodes the desired methyltransferase. The expression of natural or synthetic nucleic acids is typically achieved by operably linking a nucleic acid of interest to a promoter (which is either constitutive or inducible), incorporating the construct into an expression vector, and introducing the vector into a suitable host cell. Typical vectors contain transcription and translation terminators, transcription and translation initiation sequences, and promoters useful for regulation of the expression of the particular nucleic acid. The vectors optionally comprise generic expression cassettes containing at least one independent terminator sequence, sequences permitting replication of the cassette in eukaryotes, or prokaryotes, or both (e.g., shuttle vectors), and selection markers for both prokaryotic and eukaryotic systems. Vectors are suitable for replication and integration in prokaryotes, eukaryotes, or preferably both. See, Giliman and Smith (1979), *Gene*, 8:81–97; Roberts et al. (1987), *Nature*, 328:731–734; Berger and Kimmel, *Guide to Molecular Cloning Techniques, Methods in Enzymology*, volume 152, Academic Press, Inc., San Diego, Calif. (Berger); Sambrook et al. (1989), Molecular Cloning—A Laboratory Manual (2nd ed.) Vol. 1–3, Cold Spring Harbor Laboratory, Cold Spring Harbor Press, N.Y., (Sambrook); and F. M. Ausubel et al., Current Protocols in Molecular Biology, eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.), as well as many other commercial sources known to one of skill in the art.

The nucleic acids (e.g., promoters and vectors) used in the present method can be isolated from natural sources, obtained from such sources as ATCC or GenBank libraries, or prepared by synthetic methods. Synthetic nucleic acids can be prepared by a variety of solution or solid phase methods. Detailed descriptions of the procedures for solid phase synthesis of nucleic acids by phosphite-triester, phosphotriester, and H-phosphonate chemistries are widely available. See, for example, Itakura, U.S. Pat. No. 4,401, 796; Caruthers, et al., U.S. Pat. Nos. 4,458,066 and 4,500, 707; Beaucage, et al., (1981) *Tetrahedron Lett.*, 22:1859–1862; Matteucci, (1981) et al., *J. Am. Chem. Soc.*, 103:3185–3191; Caruthers, et al., (1982) *Genetic Engineering*, 4:1–17; Jones, chapter 2, Atkinson, et al., chapter 3, and Sproat, et al., chapter 4, in *Oligonucleotide Synthesis: A Practical Approach*, Gait (ed.), IRL Press, Washington D.C. (1984); Froehler, et al., (1986) *Tetrahedron Lett.*, 27:469–472; Froehler, et al., (1986) *Nucleic Acids Res.*, 14:5399–5407; Sinha, et al. (1983) *Tetrahedron Lett.*, 24:5843–5846; and Sinha, et al., (1984) *Nucl. Acids Res.*, 12:4539–4557, which are incorporated herein by reference.

a. In Vitro Gene Transfer

It is expected that those of skill in the art are knowledgeable in the numerous expression systems available for expression of DNA encoding DNA adenine methyltransferases. No attempt to describe in detail the various methods known for the expression of proteins in prokaryotes or eukaryotes is made here.

There are several well established methods of introducing nucleic acids into bacterial and animal cells, any of which may be used in the present invention. These include: calcium phosphate precipitation, fusion of the recipient cells with bacterial protoplasts containing the DNA, treatment of the recipient cells with liposomes containing the DNA, DEAE dextran, receptor-mediated endocytosis, electroporation, micro-injection of the DNA directly into the cells, infection with viral vectors, etc.

For in vitro applications, the delivery of nucleic acids can be to any cell grown in culture, whether of bacterial, plant or animal origin, vertebrate or invertebrate, and of any tissue or type. Contact between the cells and the genetically engineered nucleic acid constructs, when carried out in vitro, takes place in a biologically compatible medium. The concentration of nucleic acid varies widely depending on the particular application, but is generally between about 1 $\mu$mol and about 10 mmol. Treatment of the cells with the nucleic acid is generally carried out at physiological temperatures (about 37° C.) for about 1 to about 48 hours, preferably about 2 to 4 hours.

In one group of embodiments, a nucleic acid is added to 60–80% confluent plated cells having a cell density of about $10^3$ to about $10^5$ cells/mL, more preferably about $2 \times 10^4$ cells/mL. The concentration of the suspension added to the cells is preferably from about 0.01 to 0.2 μg/mL, more preferably about 0.1 μg/mL.

b. Cells to be Transformed

The compositions and methods of the present invention are used to transfer genes into a wide variety of cell types, in vivo and in vitro. Although any prokaryotic or eukaryotic cells may be used, prokaryotic cells such as *E. coli* are preferred.

C. Detection of Methyltransferase-encoding Nucleic Acids

The present invention provides methods for detecting DNA or RNA encoding DNA adenine methyltransferases. A variety of methods for specific DNA and RNA measurement using nucleic acid hybridization techniques are known to those of skill in the art. See Sambrook, et al.; Nucleic Acid Hybridization, A Practical Approach, Ed. Hames, B. D. and Higgins, S. J., IRL Press, 1985; Gall and Pardue (1969), *Proc. Natl. Acad. Sci., U.S.A.*, 63:378–383; and John et al. (1969) *Nature*, 223:582–587. The selection of a hybridization format is not critical.

For example, one method for evaluating the presence or absence of DNA encoding DNA adenine methyltransferases in a sample involves a Southern transfer. Briefly, the digested genomic DNA is run on agarose slab gels in buffer and transferred to membranes. Hybridization is carried out using the nucleic acid probes discussed above. As described above, nucleic acid probes are designed based on the nucleic acid sequences encoding methyltransferases (See SEQ ID NOs: 1, 3, 5, 7.) The probes can be full length or less than the full length of the nucleic acid sequence encoding the methyltransferase. Shorter probes are empirically tested for specificity. Preferably nucleic acid probes are 20 bases or longer in length. (See Sambrook, et al. for methods of selecting nucleic acid probe sequences for use in nucleic acid hybridization.) Visualization of the hybridized portions allows the qualitative determination of the presence or absence of DNA encoding DNA adenine methyltransferases.

Similarly, a Northern transfer may be used for the detection of mRNA encoding DNA adenine methyltransferases. In brief, the mRNA is isolated from a given cell sample using an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify the presence or absence of DNA adenine methyltransferases.

Sandwich assays are commercially useful hybridization assays for detecting or isolating nucleic acid sequences. Such assays utilize a "capture" nucleic acid covalently immobilized to a solid support and a labelled "signal" nucleic acid in solution. The clinical sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

Typically, labelled signal nucleic acids are used to detect hybridization. Complementary nucleic acids or signal nucleic acids may be labelled by any one of several methods typically used to detect the presence of hybridized polynucleotides. The most common method of detection is the use of autoradiography with $^3H$, $^{125}I$, $^{35}S$, $^{14}C$, or $^{32}P$-labelled probes or the like. Other labels include ligands which bind to labelled antibodies, fluorophores, chemiluminescent agents, enzymes, and antibodies which can serve as specific binding pair members for a labelled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The label may also allow indirect detection of the hybridization complex. For example, where the label is a hapten or antigen, the sample can be detected by using antibodies. In these systems, a signal is generated by attaching fluorescent or enzyme molecules to the antibodies or, in some cases, by attachment to a radioactive label. (Tijssen, P., "Practice and Theory of Enzyme Immunoassays," *Laboratory Techniques in Biochemistry and Molecular Biology*, Burdon, R. H., van Knippenberg, P. H., Eds., Elsevier (1985), pp. 9–20.)

The sensitivity of the hybridization assays may be enhanced through use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR), the ligase chain reaction (LCR), Qβ-replicase amplification and other RNA polymerase mediated techniques (e.g., NASBA), are found in Berger, Sambrook, and Ausubel, as well as Mullis et al. (1987), U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990), *C&EN* 36–47; *The Journal Of NIH Research* (1991), 3: 81–94; (Kwoh et al. (1989), *Proc. Nati. Acad. Sci. USA*, 86:1173; Guatelli et al. (1990), *Proc. Natl. Acad. Sci. USA*, 87:1874; Lomell et al. (1989), *J. Clin. Chem.*, 35:1826; Landegren et al. (1988), *Science*, 241:1077–1080; Van Brunt (1990), *Biotechnology*, 8:291–294; Wu and Wallace (1989), *Gene*, 4:560; Barringer et al. (1990), *Gene*, 89:117, and Sooknanan and Malek (1995), *Biotechnology*, 13:563–564. Improved methods of cloning in vitro amplified nucleic acids are described in Wallace et al., U.S. Pat. No. 5,426,039. Other methods recently described in the art are the nucleic acid sequence based amplification (NASBA™, Cangene, Mississauga, Ontario) and Q Beta Replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation.

Oligonucleotides for use as probes, e.g., in vitro amplification methods, for use as gene probes, or as inhibitor components are typically synthesized chemically according to the solid phase phosphoramidite triester method described by Beaucage and Caruthers (1981), *Tetrahedron Letts.*, 22(20):1859–1862, e.g., using an automated synthesizer, as described in Needham-Van Devanter et al. (1984), *Nucleic Acids Res.*, 12:6159–6168. Purification of oligonucleotides, where necessary, is typically performed by either native acrylamide gel electrophoresis or by anion-exchange HPLC as described in Pearson and Regnier (1983), *J. Chrom.*, 255:137–149. The sequence of the synthetic oligonucleotides can be verified using the chemical degradation method of Maxam and Gilbert (1980) in Grossman and Moldave (eds.) Academic Press, New York, *Methods in Enzymology*, 65:499–560.

An alternative means for determining the level of expression of a gene encoding an DNA adenine methyltransferase is in situ hybridization. In situ hybridization assays are well known and are generally described in Angerer, et al., *Methods Enzymol.*, 152:649–660 (1987). In an in situ hybridization assay, cells are fixed to a solid support, typically a glass slide. If DNA is to be probed, the cells are denatured with heat or alkali. The cells are then contacted with a hybridization solution at a moderate temperature to permit annealing of labeled probes specific to DNA adenine methyltransferases. The probes are preferably labeled with radioisotopes or fluorescent reporters.

d. Detection of Methyltransferase Gene Products

Methyltransferase may be detected or quantified by a variety of methods. Preferred methods involve the use of specific antibodies.

Methods of producing polyclonal and monoclonal antibodies are known to those of skill in the art. See, e.g., Coligan (1991), Current Protocols in Immunology, Wiley/Greene, NY; and Harlow and Lane (1989), Antibodies: A Laboratory Manual, Cold Spring Harbor Press, NY; Stites et al. (eds.) Basic and Clinical Immunology (4th ed.) Lange Medical Publications, Los Altos, Calif., and references cited therein; Goding (1986), Monoclonal Antibodies: Principles and Practice (2d ed.) Academic Press, New York, NY; and Kohler and Milstein (1975), *Nature,* 256:495–497. Such techniques include antibody preparation by selection of antibodies from libraries of recombinant antibodies in phage or similar vectors. See, Huse et al. (1989), *Science,* 246:1275–1281; and Ward et al. (1989), *Nature,* 341:544–546. For example, in order to produce antisera for use in an immunoassay, the polypeptide of SEQ ID NO: 2, 4, 6, or 8, or a fragment thereof, is isolated as described herein. For example, recombinant protein is produced in a transformed cell line. An inbred strain of mice or rabbits is immunized with the protein of SEQ ID No. 2, 4, 6, or 8, or a fragment thereof, using a standard adjuvant, such as Freund's adjuvant, and a standard immunization protocol. Alternatively, a synthetic peptide derived from the sequences disclosed herein and conjugated to a carrier protein can be used as an immunogen. Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against non-adenine methyltransferases or even other adenine methyltransferases, using a competitive binding immunoassay. Specific monoclonal and polyclonal antibodies and antisera will usually bind with a $K_D$ of at least about 0.1 mM, more usually at least about 1 $\mu$M, preferably at least about 0.1 $\mu$M or better, and most preferably, 0.01 $\mu$M or better.

A number of immunogens may be used to produce antibodies specifically reactive with DNA adenine methyltransferases. Recombinant protein is the preferred immunogen for the production of monoclonal or polyclonal antibodies. Naturally occurring protein may also be used either in pure or impure form. Synthetic peptides made using the DNA adenine methyltransferase sequences described herein may also used as an immunogen for the production of antibodies to the protein. Recombinant protein can be expressed in eukaryotic or prokaryotic cells as described above, and purified as generally described above. The product is then injected into an animal capable of producing antibodies. Either monoclonal or polyclonal antibodies may be generated, for subsequent use in immunoassays to measure the protein.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the titer of reactivity to the DNA adenine methyltransferase. When appropriately high titers of antibody to the immunogen are obtained, blood is collected from the animal and antisera are prepared. Further fractionation of the antisera to enrich for antibodies reactive to the protein can be done if desired. (See Harlow and Lane, supra).

Monoclonal antibodies may be obtained by various techniques familiar to those skilled in the art. Briefly, spleen cells from an animal immunized with a desired antigen are immortalized, commonly by fusion with a myeloma cell (See, Kohler and Milstein, *Eur. J. Immunol.* 6:511–519 (1976), incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al. (1989) *Science* 246:1275–1281.

A particular protein can be measured by a variety of immunoassay methods. For a review of immunological and immunoassay procedures in general, see *Basic and Clinical Immunology* 7th Edition (D. Stites and A. Terr ed.) 1991. Moreover, the immunoassays of the present invention can be performed in any of several configurations, which are reviewed extensively in *Enzyme Immunoassay,* E. T. Maggio, ed., CRC Press, Boca Raton, Fla. (1980); "Practice and Theory of Enzyme Immunoassays," P. Tijssen, *Laboratory Techniques in Biochemistry and Molecular Biology,* Elsevier Science Publishers B. V. Amsterdam (1985); and Harlow and Lane, *Antibodies, A Laboratory Manual,* supra, each of which is incorporated herein by reference.

Immunoassays to methyltransferases of the present invention may use a polyclonal antiserum which was raised to the protein of SEQ ID NO: 2, 4, 6, or 8, or a fragment thereof. This antiserum is selected to have low crossreactivity against other (non-methyltransferase or methyltransferase) proteins and any such crossreactivity is removed by immunoabsorbtion prior to use in the immunoassay.

In addition, it is possible to produce monospecific antibodies that react to specific DNA methyltransferases from specific species of bacteria as identified herein. Monospecific antibodies are achieved by appropriate cross-absorption with select DNA methyltransferases or by raising antibodies against species specific regions of the amino acid sequence of the transferases. Such unique peptide fragments are routinely identified by sequence comparisons.

In order to produce antisera for use in an immunoassay, the protein of SEQ ID NO: 2, 4, 6, or 8, or a fragment thereof, is isolated as described herein. For example, recombinant protein is produced in a transformed cell line. An inbred strain of mice such as balb/c is immunized with the protein of SEQ ID NO: 2 using a standard adjuvant, such as Freund's adjuvant, and a standard mouse immunization protocol. Alternatively, a synthetic peptide derived from the sequences disclosed herein and conjugated to a carrier protein can be used as an immunogen. Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against non-adenine methyltransferases, using a competitive binding immunoassay such as the one described in Harlow and Lane, supra, at pages 570–573.

Immunoassays in the competitive binding format can be used for the crossreactivity determinations. For example, the protein of SEQ ID NO: 2 can be immobilized to a solid support. Proteins (other methyltransferases, or non-methyltransferases) are added to the assay which compete with the binding of the antisera to the immobilized antigen. The ability of the above proteins to compete with the binding of the antisera to the immobilized protein is compared to the protein of SEQ ID NO: 2. The percent crossreactivity for the above proteins is calculated, using standard calculations. Those antisera with less than 10% crossreactivity with each of the proteins listed above are selected and pooled. The cross-reacting antibodies are optionally removed from the pooled antisera by immunoabsorbtion with the above-listed proteins.

The immunoabsorbed and pooled antisera are then used in a competitive binding immunoassay as described above to compare a second protein to the immunogen protein, in this case, the adenine methyltransferase of SEQ ID NO: 2. In order to make this comparison, the two proteins are each assayed at a wide range of concentrations and the amount of each protein required to inhibit 50% of the binding of the antisera to the immobilized protein is determined. If the amount of the second protein required is less than 10 times the amount of the protein of SEQ ID NO: 2 that is required, then the second protein is said to specifically bind to an antibody generated to an immunogen consisting of the protein of SEQ ID NO: 2.

The presence of a desired polypeptide (including peptide, transcript, or enzymatic digestion product) in a sample may be detected and quantified using Western blot analysis. The technique generally comprises separating sample products by gel electrophoresis on the basis of molecular weight, transferring the separated proteins to a suitable solid support (such as a nitrocellulose filter, a nylon filter, or derivatized nylon filter), and incubating the sample with labeling antibodies that specifically bind to the analyte protein. The labeling antibodies specifically bind to analyte on the solid support. These antibodies are directly labeled, or alternatively are subsequently detected using labeling agents such as antibodies (e.g., labeled sheep anti-mouse antibodies where the antibody to an analyte is a murine antibody) that specifically bind to the labeling antibody.

3. Purification of DNA Adenine Methyltransferases

The polypeptides of this invention may be purified to substantial purity by standard techniques, including selective precipitation with such substances as ammonium sulfate, column chromatography, immunopurification methods, and others. See, for instance, R. Scopes, *Protein Purification: Principles and Practice,* Springer-Verlag: New York (1982), incorporated herein by reference. For example, the methyltransferase proteins and polypeptides produced by recombinant DNA technology may be purified by a combination of cell lysis (e.g., sonication) and affinity chromatography or immunoprecipitation with a specific antibody to methyltransferase. For fusion products, subsequent digestion of the fusion protein with an appropriate proteolytic enzyme releases the desired polypeptide. The proteins may then be further purified by standard protein chemistry techniques. A specific protocol for purifying the methyltransferases of this invention is provided in Example 1(e).

4. Screening for Inhibitors of Methyltransferase or Associated Gene Expression

The methyltransferase genes identified herein provide novel targets for screening for agents that attenuate, inhibit, or interfere with the viability of the pathogens bearing with the gene. Inhibition (i.e. blocking) or complete elimination of the expression of the methyltransferase gene or genes described herein results in a mitigation or elimination of the ability of the subject bacteria to infect and/or grow and/or proliferate in an animal or plant host as compared to the same stain of bacteria (or virus) in which there is no inhibition or elimination of the virulence-related gene or gene product.

Having provided herein genes whose expression is required for viability of pathogenic bacteria, it is possible to screen for agents and/or for drugs that, by blocking the activity of the methyltransferase gene, mitigate the virulence of the target pathogen.

Antibiotics and other synthetic drugs targeted to specific proteins generally act by interacting with and inhibiting the activity of the target protein. The methyltransferase enzymatic activity assays provided herein are useful to identify inhibitors of that activity. To do so, the enzymes capacity to methylate a nucleic acid is assayed in the presence and absence of a test substance, such as a synthetic or isolated naturally occurring chemical inhibitor (in particular peptides or other ligands that bind to the active site or to allosteric sites of the methyltransferase enzyme). An inhibitor of the transferase depresses the activity of enzyme at least 50%, preferably at least 90%, and most preferably at least 99%.

The methyltransferase genes or gene product (i.e., mRNA) is preferably detected and/or quantified in a biological sample. As used herein, a biological sample is a sample of biological tissue or fluid that, in a healthy and/or pathological state, contains methyltransferase encoding nucleic acid or the polypeptide. Such samples include, but are not limited to, sputum, amniotic fluid, blood, blood cells (e.g., white cells), tissue or fine needle biopsy samples, urine, peritoneal fluid, and pleural fluid, or cells therefrom. For plants, root tissue or leaf tissue can be used. Biological samples may also include sections of tissues such as frozen sections taken for histological purposes.

The present invention encompasses developing antisense protocols, antibiotics and antagonists that specifically inhibit the methyltransferase activity of the identified enzymes or the expression of the genes of this invention. The detection and testing of such inhibitors is made possible by the ability to make and obtain the claimed enzyme using methods described herein.

Antisense agents are used to reduce or eliminate methyltransferase activity. Antisense agents include fragments or the methyltransferase genes that are operably linked in reverse orientation to an efficient promoter. Also included in antisense agents are ribozymes such as the hairpin or hammerhead types. For antisense agents suitable assays involve detecting the presence, absence, or quantity or amount of transcript of the gene or gene product. Northern blots, quantitative PCR or immunoassays are all suitable for detection of the effectiveness of antisense agents.

In still another embodiment, bacterial reporter strains are used to evaluate candidate anti-transferase agents. In such assays, recombinant bacteria are modified to include a reporter gene attached to a nucleic acid encoding the methyltransferase gene. When the genes are expressed, the reporter gene is also expressed and provides a detectable signal indicating the expression of the gene. Anti-methyltransferase agent screens then involve contacting the reporter strains and/or cells, tissues, or organisms prior to or after infection with the reporter strains and subsequently detecting expression levels of the reporter gene.

In addition to screening for antisense agents, this invention provides for methods that facilitate the identification of non-antisense drug candidates especially under conditions of high throughput. The screening for such non-nucleic acid based inhibitory agents commonly involves contacting the target pathogen (e.g. *Brucella abortus*), and /or a tissue containing the pathogen, and/or an animal, with one or more candidate anti-methyltransferase agents and detecting the presence absence, quantity of the gene product. Alternatively, candidate anti-methyltransferase agents can be identified simply by their ability to bind to the gene or gene product and inhibit its biological activity.

Methods for detecting the biological activity of the methyltransferases are provided herein and include reaction conditions and suitable substrates for methylation. These assays can be used to screen for anti-methyltransferase agents. Absence of the activity of the gene during and/or after contacting of the bacteria, a cell, a tissue, and/or an organism with an anti-transferase agent of interest will indicate that the particular test compound is a likely candidate for an antibiotic.

In view of the foregoing, preferred assays for detection anti-methyltransferase agents fall into the following categories:

i) Detection of gene or gene-derived nucleic acid presence, absence, or quantity;

ii) Screening for agents that bind to a gene or gene derived nucleic acid;

iii) Detection of a virulence gene derived polypeptide;

iv) Detection of binding of a prospective agent to gene derived polypeptides;

v) Use of bacterial reporter strains; and, vi) Detection of the biological activity of the transferase gene.

5. High-Throughput Screening of Candidate Agents that Block Methyltransferase Activity Conventionally, new chemical entities with useful properties are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of potential therapeutic compounds (candidate compounds). Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

a. Combinatorial Chemical Libraries

Recently, attention has focused on the use of combinatorial chemical libraries to assist in the generation of new chemical compound leads. A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) 37(9): 1233–1250).

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.,* 37: 487–493, Houghton et al. (1991) *Nature,* 354: 84–88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, Dec. 26, 1991), encoded peptides (PCT Publication WO 93/20242, Oct. 14, 1993), random bio-oligomers (PCT Publication WO 92/00091, Jan. 9, 1992), benzodiazepines (U.S. Pat. No. 5,288,514), diversomers such as hydantoins, benzodiazepines and dipeptides (Hobbs et al., (1993) *Proc. Nat. Acad. Sci. USA* 90: 6909–6913), vinylogous polypeptides (Hagihara et al. (1992) *J. Amer. Chem. Soc.* 114: 6568), nonpeptidal peptidomimetics with a Beta-D-Glucose scaffolding (Hirschmann et al., (1992) *J. Amer. Chem. Soc.* 114: 9217–9218), analogous organic syntheses of small compound libraries (Chen et al. (1994) *J. Amer. Chem. Soc.* 116: 2661), oligocarbamates (Cho, et al., (1993) *Science* 261:1303), and/or peptidyl phosphonates (Campbell et al., (1994) *J. Org. Chem.* 59: 658). See, generally, Gordon et al., (1994) *J. Med. Chem.* 37:1385, nucleic acid libraries, peptide nucleic acid libraries (see, e.g., U.S. Pat. No. 5,539,083) antibody libraries (see, e.g., Vaughn et al. (1996) *Nature Biotechnology,* 14(3): 309–314), and PCT/US96/10287), carbohydrate libraries (see, e.g., Liang et al. (1996) *Science,* 274: 1520–1522, and U.S. Pat. No. 5,593,853), and small organic molecule libraries (see, e.g., benzodiazepines, Baum (1993) C&EN, Jan 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. No. 5,506,337, benzodiazepines 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.;

Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

b. High Throughout Assays of Chemical Libraries

Any of the assays for compounds inhibiting the virulence described herein are amenable to high throughput screening. As described above, having identified the nucleic acid associated with virulence, likely drug candidates either inhibit expression of the gene product, or inhibit the activity of the expressed protein. Preferred assays thus detect inhibition of transcription (i.e., inhibition of mRNA production) by the test compound(s), inhibition of protein expression by the test compound(s), or binding to the gene (e.g., gDNA, or cDNA) or gene product (e.g., mRNA or expressed protein) by the test compound(s). Alternatively, the assay can detect inhibition of the characteristic activity of the gene product or inhibition of or binding to a receptor or other transduction molecule that interacts with the gene product.

High throughput assays for the presence, absence, or quantification of particular nucleic acids or protein products are well known to those of skill in the art. Similarly, binding assays are similarly well known. Thus, for example, U.S. Pat. No. 5,559,410 discloses high throughput screening methods for proteins, U.S. Pat. No. 5,585,639 discloses high throughput screening methods for nucleic acid binding (i.e., in arrays), while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high thruput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

6. Methyltransferase Activity

This protocol exemplifies a method for assaying for methyltransferase activity. It is a particularly good method because it allows for the detection of processivity but it need not be so used.

A hemimethylated DNA substrate containing two (2) GANTC methylation sites, for example the $N^6$60/66-mer described in Example 5(b) below, is used to address the processivity of CcrM. The GANTC sites are resistant to HinfI digestion but susceptible to HindII digestion when hemimethylated. However, upon enzymatic methylation, the GANTC sites become fully methylated and resistant to HindII digestion. The methylation sites in the hemimethylated $N^6$60/66-mer substrate are asymmetrically spaced so that DNA fragments of differing sizes are obtained upon HindII digestion. Thus, one can address the preference for initial methylation by the enzyme during processive DNA methylation.

The $N^6$60/66-mer was 5'-labeled using T4 polynucleotide kinase and $[\gamma^2P]$-ATP according to the manufacturer's protocol (U.S.Biochemical). Unreacted $[\gamma^2P]$-ATP and T4 polynucleotide kinase were separated from labeled duplex DNA by eluting the DNA through a 1-mL G-25 gel filtration column. Methylation assays were performed using 250 nM CcrM, 2 $\mu$M 5'-labeled $N^6$60/66-mer, 6 $\mu$M [$^3$H]-SAM in the appropriate reaction buffer at 30° C. 5 $\mu$L of reaction was quenched with 500 $\mu$L 10% perchloric acid, 200 $\mu$L saturated sodium pyrophosphate, and 20 $\mu$L single-stranded DNA at times varying from 15 seconds to 20 minutes. These reactions were placed on ice for at least 30 minutes, and then were subjected to the filter binding assay monitoring [$^3$H]-CH$_3$ incorporation from [$^3$H]-SAM into duplex DNA as described in Example 5.

Concomitantly, 20 $\mu$L reaction aliquots were quenched by either heat denaturation of CcrM or by the addition of 50 $\mu$L phenol/chloroform at times varying from 15 seconds to 20 minutes. The quenched reactions were then subjected to HindII digestion. Typically, these reactions consisted of 10 $\mu$L of the quenched DNA in a 20 $\mu$L reaction with the appropriate reaction buffer and 1 $\mu$L of HindII. After three hours of HindII digestion at 37° C., 10 $\mu$L of this reaction was quenched with 10 $\mu$L of gel loading dye. DNA fragments were then resolved by 16% denaturing gel electrophoresis followed by PhosphorImaging to identify cleavage patterns.

Results from the [$^3$H]-SAM assay indicate that two mole equivalents of [$^3$H]-CH$_3$ were incorporated into the $N^6$60/66-mer after 20 minutes. By direct contrast, only one mole equivalent of [$^3$H]-CH$_3$ is incorporated into the $N^6$23/30-mer or $N^6$45/50-mer after 20 minutes under identical conditions. Results from the HindII digestion assay reveal fully protected DNA substrate ($N^6$60/66-mer) after 20 minutes, indicating that DNA had been methylated at both GANTC sites. Furthermore, no intermediate products were obtained, i.e., methylation at a single GANTC site, indicating that under the assay conditions used the enzyme processively methylated both CANTC sites on the same DNA substrate. Approximately 250 nM of processively methylated DNA was detected after PhosphorImaging quantitation, consistent with results from the tritium incorporation assay.

EXAMPLES

The examples provided herein are provided by way of illustration only and not by way of limitation. Those of skill will readily recognize a variety of noncritical parameters which could be changed or modified to yield essentially similar results.

Example 1

SEQ ID NO:1: Rhizobium Methyltransferase Sequence a. Isolation

The *Rhizobium meliloti* ccrM gene (Rhizobium ccrM) was isolated by generating specific probes to Rhizobium ccrM using the Polymerase Chain Reaction (PCR) and using them to screen a *R. meliloti* lambda library. The primers used to generate the probe had the following sequence:

Forward primer (IFADDPPY): 5'-ATY TTY GCB GAY CCB CCB TA (SEQ ID NO:9)

Forward primer 1 (LDPFFG): 5'-CCR AAR AAV GGR TCS AG (SEQ ID NO:10)

Forward primer 2 (IGIERE): 5'-TCV CGY TCR ATV CCR AT (SEQ ID NO:11)

Forward primer and reverse primer 1 amplify a 570 bp fragment. Forward primer and reverse primer 2 amplify a 635 bp fragment. The R. meliloti lambda library was obtained and subsequent screening was accomplished as described in Sambrook et al.

Three positive clones were isolated from the library. The complete Rhizobium ccrM gene was isolated as a 3.0 kb NotI fragment and has been completely sequenced in both directions (SEQ ID NO:1). The gene encodes a protein having SEQ ID NO:2.

b. Homology Between the Caulobacter and Rhizobium ccrM Methyltransferase Genes

The deduced sequences of the Rhizobium and Caulobacter ccrM genes were compared, revealing 61% identity and 74% similarity. FIG. 9. The homology is present throughout the two sequences, particularly around regions which had been previously identified as important to the function of other known adenine DNA methyltransferases. However, there are regions of divergence, especially around the N- and C-termini.

The DNA methyltransferase M. HinfI from *Haemophilus influenzae* has the same recognition sequence (GANTC) as CcrM and is part of a restriction modification system in this bacteria (Chandrasegaran et al., *Gene* 70:387–392, 1988). It should be noted that *H. influenzae* is not part of the alpha subdivision of gram negative bacteria and therefore it is likely that this DNA methyltransferase evolved separately from the ccrM family. The deduced sequences derived from the Rhizobium and Caulobacter ccrM genes were compared to the M. HinfI sequence and it was found, as predicted, that the Caulobacter and Rhizobium genes are much more closely related to each other than to the M. HinfI DNA methyl-transferase.

% similarity between the Rhizobium (Rh), Caulobacter (Cc) Brucella, Hp=*Helicobacter pylori* and M. HinfI (Hf) CcrM proteins

|    | Cc  | Rh | Br | Hf | Hp |
|----|-----|----|----|----|----|
| Cc | 100 | 74 | 82 | 66 | 57 |
| Rh |     |    | 90 | 64 | 53 |
| Br |     |    |    | 66 | 54 |
| Hf |     |    |    |    | 71 |

C. Rhizobium ccrM is Essential in Rhizobium

Previous work by Stephens et al., *Proc. Nati. Acad. Sci.* 93:1210–1214, (1996) has demonstrated that the Caulobacter ccrM is essential for viability in Caulobacter. Therefore it is of interest to determine whether other ccrM homologs are also essential.

The coding sequence of the Rhizobium ccrM was disrupted by insertion of the gene encoding kanamycin/neomycin resistance (a selectable marker) into the middle of the gene. This construct was cloned into a suicide plasmid that under selection integrates into the Rhizobium ccrM locus. The result of this integration is that the wild-type copy is separated from the disrupted copy by the vector sequence, which includes the sacB gene. Growth of Rhizobium containing an active sacB gene on sucrose is lethal (Hynes et al., *Gene* 78:111–120, 1989). This enables selection for the second recombination event between the disrupted and wild-type copy of ccrM by growth on sucrose. Selection for the event in which only the disrupted copy remained at the ccrM locus occurred only in the presence of a functional copy of ccrM on a replicating plasmid. Thus the Rhizobium ccrM gene is essential for viability in Rhizobium.

| Strain  | Plasmid        | ccrM::nptII | ccrM + |
|---------|----------------|-------------|--------|
| LS2590  | none           | 0           | 300    |
| LS2591  | none           | 0           | 300    |
| LS2590  | pMB440         | 0           | 300    |
| LS2591  | pMB440         | 0           | 300    |
| LS2590  | pRW175 (ccrM +)| 145         | 105    |
| LS2591  | pRW175 (ccrM +)| 192         | 58     |

The Rhizobium ccrM locus can only be disrupted if ccrM is present in trans.

d. Overexpression of the Rhizobium ccrM Gene Results in Defects in Cell Division and Cell Morphology Caulobacter goes to great lengths to ensure that CcrM is presently only at a specific time of the cell cycle, by regulating the availability of CcrM at two levels: transcription and protein turnover (Stephens et al., *J. Bacteriol.* 177:1662–1669, 1995; Wright et al., *Genes and Development* 10:1532–1542, 1996). If this regulation is perturbed by expressing ccrM throughout the cell cycle, the cells exhibit defects in cell division, cell morphology, and the initiation of DNA replication (Zweiger et al., *J. Mol. Biol.* 235: 472–485, 1994; Wright et al., *Genes and Development* 10:1532–1542, 1996). Thus it is important to ensure that CcrM is only present in predivisional stage of the Caulobacter cell cycle. We were therefore interested to determine what would happen if the Rhizobium ccrM gene were expressed at high levels in Rhizobium.

The 3.0 kb NotI fragment encompassing the Rhizobium ccrM gene was ligated into a high copy number plasmid and this construct was mated into wild-type Rhizobium. The phenotype of the resulting strain is clearly abnormal compared to wild-type. Wild type Rhizobium is a short rod-shaped cell; however, the cells of the strain in which ccrM was overexpressed are much larger and are highly branched. The branching points appear to occur randomly and vary dramatically between cells. This phenotype is similar to that observed when the cell division gene ftsZ is overexpressed in Rhizobium (B. Margolin, personal communication).

Interestingly, if the Rhizobium ccrM gene is placed in the high copy number plasmid such that it is driven by an additional promoter from the plasmid, no transformants were obtained in Rhizobium. This suggests that the cells can tolerate, to a certain extent, an elevated level of CcrM, but there is a point at which the level of ccrM in the cell becomes lethal.

As CcrM is only present at a specific time in the Caulobacter cell cycle, hemimethylated DNA can be detected in mixed cell cultures. When ccrM is expressed throughout the cell cycle, whether in a Ion null mutant or from expression from a constitutively transcribed promoter, only fully methylated DNA can be detected. It was of interest to determine whether hemimethylated DNA could be detected in Rhizobium, which would suggest that the Rhizobium ccrM is also cell cycle regulated. A naturally occurring restriction site which overlaps a HinfI site and is sensitive to adenine methylation was identified in Rhizobium. The DNA methylation state at that site was determined and hemimethylated DNA was detected. For a detailed explanation of this experiment see Zweiger et al., *J. Mol. Biol.* 235: 472–485, (1994). The detection of hemimethylated DNA could be due to either protection from being methylated by a protein binding at that site or the Rhizobium CcrM being present only at a specific time in the cell cycle.

e. Enzyme Purification

BL21(DE3) hosting pCS255b was streaked from glycerol stock onto an SB (30 g tryptone, 20 g yeast extract, 10 g MOPS, pH 7.5) agar plate containing 200 μg/ml amp, and maintained at 37° C. Each 1 L SB/amp (200 μg/mL) culture was inoculated with one single colony at 37° C. until $OD_{600}$~0.8. Each cell culture was then induced with 0.5 mM IPTG at 37° C. for 1.5–2 hours.

The cells were harvested by centrifugation at 12000 rpm at 4° C. for 20 minutes. Approximately 20 grams of cell paste was obtained from 5 liters of culture. The cells were resuspended in a 25 mM HEPES, pH 7.5, 1 mM EDTA, 5 mM β-mercaptoethanol, 1 mg/mL lysozyme, and 0.1% PMSF 10% glycerol, and lysed by sonication using a 50% duty cycle. The process involved sonicating for 30 seconds, stirring the cells for 90 seconds, and repeating the process until the solution was very viscous. This solution was then centrifuged at 12,000 rpm for 20 minutes at 4° C., followed by ultracentrification at 40,000 rpm at 4° C. for 2 hours.

The supernatant was diluted 5-fold with Buffer A (25 mM HEPES, pH 7.5, 5 mM β-ME, 1 mM EDTA, 10% glycerol) and applied to a 30×2.5 cm DEAE-Sephacel connected to a P11 phosphocellulose column pre-equilibrated with 1 L of buffer A. CcrM does not bind to DEAE-Sephacel while 90% of the proteins from the cell lysate do. The two connected columns were washed with 500 mL buffer A. The P11 column was then disconnected from the DEAE column and eluted with a linear gradient of 1 L buffer A with 25 to 750 mM NaCl. CcrM was eluted at ~300 mM NaCl. Fractions were collected and analyzed for protein content by Abs280 as well as by SDS-PAGE.

After elution of the protein from the phosphocellulose column, the enzyme was concentrated using an Amicon apparatus employing a YM-30 molecular weight cut-off membrane. After concentration, the protein was determined to be >95% pure based upon SDS-polyacrylamide gel electrophoresis. The concentration of the protein was first measured using the Bradford colorimetric technique (Bradford, *Anal. Biochem.* 72, 248–254 (1976)). The second method for determining the concentration of CcrM utilizes measuring the ultraviolet-visible spectroscopy absorbance of the protein at a wavelength of 280 nm. The extinction coefficient of the protein was determined from the predicted amino acid composition (Zweiger et al., *J. Mol. Biol.* 245, 472–485 (1994)) using the method of Gill and von Hippel *Anal. Biochem.* 182, 319–326 (1989)). The concentration of CcrM based upon this method is in excellent agreement with the concentration based on the Bradford method.

f. Rhizobium CcrM is Degraded in a Lon Protease-dependent Process as Has Been Shown in Caulobacter (Wright et al., Genes and Development 10:1532–1542, 1996).

Lon is a conserved phylogenetically widespread serine protease involved in the degradation of abnormal proteins. We generated a Lon null mutation in *Caulobacter crescentus* and demonstrated that ccrM transcription is still temporally regulated, but that it is present throughout the cell cycle, resulting in a fully methylated chromosome throughout the cell cycle, causing developmental defects (Wright et al., *Genes and Development* 10:1532–1542, 1996). Using similar methods as described in Wright et al., we expect that Rhizobium CcrM is degraded in a Lon protease-dependent process as has been shown in Caulobacter.

Example 2

Brucelia abortus Methyltransferase Sequence

The Brucella ccrM gene was isolated using the same strategy and primers as that described for isolating the Rhizobium ccrM gene, but using a Brucella gene library. A specific probe to the Brucella ccrM gene generated by PCR using the above mentioned primers was used to screen a Brucella lambda library and three clones were isolated.

Restriction mapping of these clones demonstrated that they all contained the full length ccrM gene. A 2.0 kb HindII fragment isolated from one of the positive clones which contained the complete Brucella ccrm gene was sequenced (FIGS. 3 and 4). As with the Rhizobium ccrM gene, the deduced sequence of the Brucella gene exhibits very high homology to both the Caulobacter and Rhizobium ccrM genes and lower homology to the M. HinfI DNA methyltransferase (FIG. 9).

Example 3

*Agrobacterium tumefaciens* Methyltransferase Sequence

Figure 6:
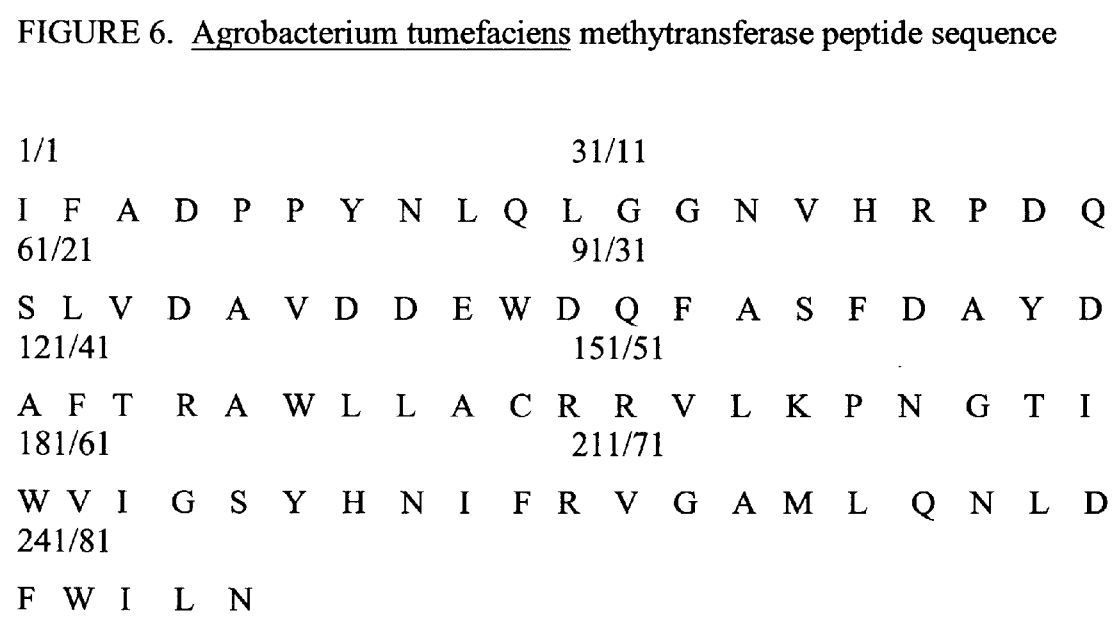

The *Agrobacterium tumefaciens* ccrM gene was isolated using the same strategy as that described for isolating the Rhizobium and Brucella ccrM gene, but using an Agrobacterium gene library. A partial gene and protein sequence are summarized in FIGS. 5 and 6.

Example 4

*Helicobacter pylori* Methyltransferase Sequence

*Helicobacter pylori* is a small, microaerophilic Gram-negative organism which can colonize the human stomach. It is a causative agent of chronic gastritis and peptic ulcer disease, and *H. pylori* infection has also been epidemiologically correlated with increased risk of gastric carcinoma and lymphoma.

*H. pylori* belongs to the epsilon subdivision of proteobacteria, and is thus evolutionarily separated from *Caulobacter crescentus, Rhizobium meliloti,* and *Brucella abortus,* all of which belong to the alpha subdivision.

The gene for the *H. pylori* homolog of CcrM has been cloned and sequenced. Unlike the other ccrM homologs cloned so far, the *H. pylori* gene has a large open reading frame located immediately downstream. The sequencing of this open reading frame is still in progress. There is high homology between the *H. pylori* CcrM homolog and the M.HinfI methyltransferase from *Haemophilus influenzae.* Because there is extensive precedent for finding close genetic linkage between methyltransferases and their cognate restriction endonucleases in Type II restriction-modification systems such as HinfI, it is likely that this open reading frame encodes a restriction endonuclease.

Because of the function of methyltransferases in such restriction-modification systems (i.e. protecting native host DNA from digestion by the cognate restriction endonuclease), it is also likely that absence of the functional methyltransferase will prove lethal to *H. pylori.*

The *Helicobacter pylori* ccrM gene was isolated using the same strategy as that described for isolating the above ccrM genes, but using a Helicobacter library. The gene and protein sequence are provided in FIGS. 7 and 8.

Example 5

Assay for Methyltransferase

The present invention also comprises efficient assays for determining methyltransferase activity.

a. Materials

[$^3$H]-S-Adenosyl methionine ([$^3$H]-SAM), [γ-$^{32}$P]ATP, and [α-$^{32}$P]-dATP were from New England Nuclear. Phosphoramidites for DNA synthesis were obtained from Glenn Research with the exception of the N[6]-methyl-deoxyadenosine phosphoramidite which was obtained from Pharmacia. Restriction and DNA-modifying enzymes used during molecular cloning and DNA manipulation experiments were generally from New England Biolabs, Promega, United States Biochemical, or Boehringer Mannheim. All other materials were obtained from commercial sources and were of the highest available quality.

The CcrM used in the following assays was obtained by the purification protocol described essentially in Example 1.e.

b. In Vitro Assays

Methyltransferase activity of CcrM was assayed by two distinct methods. in the first method, restriction assays were used to test methylation of restriction sites. The amount of DNA that is resistant to cleavage by restriction enzyme digest due to hemi- or full methylation of either the small DNA substrate or the pUC18 plasmid can be accurately monitored. If the DNA is hemi- or fully methylated by CcrM, the restricted enzyme is unable to cleave the DNA molecule and full length starting material will be obtained. If the DNA is cleaved by the restriction enzyme, smaller DNA fragments will be obtained and indicate a lack of methyl incorporation into the oligonucleotide.

The sequences of the DNA substrates were derived from the upstream sequence from the dnaA promoter. The sequence of the dnaA promoter has been published (Zweiger et al., *J. Mol. Biol.* 235: 472–485, 1994). The following is a list of substrates that were used (this list is not meant to be exhaustive):

17/23 mer DNA substrate:

5' actcgcgaqtcaacaga 3' (SEQ ID NO:12)

3' gagcgctcaqttqtctttatcgg 5' (SEQ ID NO:13)

23/30-mer

5+-TCC TCT CGC GAG TCA ACA GAA AT (SEQ ID NO:14)

3'-AGG AGA GCG CTC AGT TGT CTT TAT AGG CGC (SEQ ID NO:15)

N[6]23/30-mer

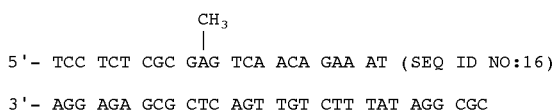

N[6]23/N[6]30-mer

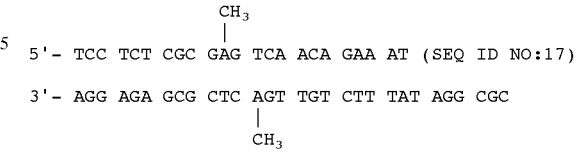

45/50-mer

5'-ATC CTC TCG CGA GTC AAC AGA AAT ATC CGC TCA TCA CCG CAA GTT (SEQ ID NO:18)

3'-AG GAG AGC GCT CAG TTG TCT TTA TAG GCG AGT AGT GGC GTT CAA TAG GCA A (SEQ ID NO:19)

N[6]45/50-mer

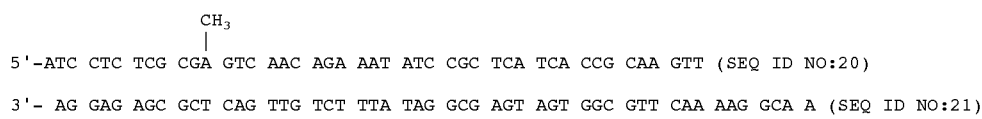

60/66-mer

5'-ATC CTC TCG CGA GTC AAC AGA AAT ATC CGC GAG TCA CCG CAA GTT TTC CGT TTG ACC GGC (SEQ ID NO:22)

3'-AG GAG AGC GCT CAG TTG TCT TTA TAG GCG CTC AGT GGC GTT CAA AAG GCA AAC TGG CCG TGG GAG G (SEQ ID NO:23)

N[6]60 /66-mer

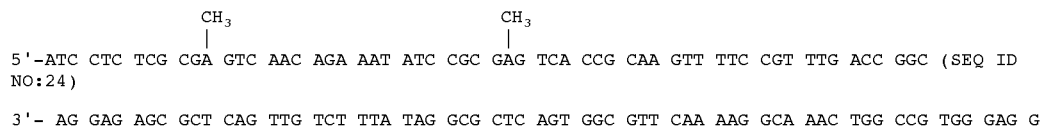

All synthetic oligonucleotides were synthesized using a DNA synthesizer and were purified as previously described by Capson et al., *Biochemistry* 31, 10984–10994 (1992)). Small duplex DNA substrates (23/30-mer) were prepared by the protocol of Kuchta et al., *Biochemistry* 26, 8410–8417 (1987)).

Larger DNA substrates (60/66-mer and N[6]60/66-mer) were prepared using a modification of the protocol established by Kaboord and Benkovic, *Proc. Natl. Acad. Sci. USA* 90, 10881–10885 (1993). Briefly, each single-strand DNA component was constructed by first 5' labeling one oligonucleotide. After ensuring that the labeling reaction was greater than 95% complete, the labeled oligonucleotide was annealed with the second oligonucleotide and a small linker oligonucleotide to bridge the gapped region. The two oligonucleotides were then ligated in the presence of T4 DNA ligase and MgATP. The linker oligonucleotide was separated from the ligated oligonucleotide by denaturing gel electrophoresis. The complementary large strand was constructed in an identical manner. Following purification of each respective large oligonucleotide, the two strands were annealed and purified by nondenaturing gel electrophoresis described by Capson et al., *Biochemistry* 31, 10984–10994 (1992). All duplex DNA were quantitated as described by Kuchta et al., *Biochemistry* 26, 8410–8417 (1987).

Analysis of DNA cleavage depends upon the nature of the DNA substrate. Small duplex DNA substrates can be 5' end-labeled using bacteriophage T4 polynucleotide kinase and [γ-$^{32}$P]ATP as the phosphate source. Both cleaved and uncleaved DNA are resolved by 20% denaturing gel electrophoresis followed by phosphorimaging techniques to analyze for product formation, i.e., cleavage of the larger duplex DNA. Furthermore, accurate quantitation of the reaction products was obtained by manipulation of the PhosphorImager software.

A typical assay for the methyltransferase activity of CcrM was performed incubating 50 nM CcrM with 1 μM 5'-labeled DNA while maintaining the concentration of S-adenosyl methionine (SAM) at 20 μM. The reaction was performed in a buffer consisting of 50 mM Tris-HCl, pH 7.5 and 5 mM β-mercaptoethanol (β-ME) with 150 mM potassium acetate at 30° C. 10 μL aliquots of the methylation reaction were quenched at variable times from 30 seconds to 10 minutes with 10 μL 1 N HCl, extracted with 40 μL of phenol/chloroform, and neutralized with 3 M NaOH in 1 M Tris. The methylated DNA was then subjected to restriction digest by either HinfI or HindII. Each reaction contained a final concentration of 100 nM reacted DNA in the presence of 1 unit/μL of HinfI or HindII in the appropriate reaction buffer supplied by the manufacturer at 37° C. After 30 minutes, 10 μL of reaction mixture was quenched with 10 μL of gel loading buffer (10% formamide, 0.25% bromophenol blue, and 0.25% xylene cyanol FF). 10 μL of this solution was then run on a 20% sequencing gel to visualize both protection and degradation of the 23/30-mer DNA as a function of time. Product formation was quantitated by measuring the ratio of uncleaved substrate and cleaved product. The ratios of substrate protection are corrected for substrate in the absence of CcrM. Corrected ratios are then multiplied by the concentration of total DNA used in each assay to yield the amount of DNA protected.

Enzymatic assays were also performed using plasmid pUC18 DNA substrate under similar reaction conditions described above. Reaction products using the larger pUC18 substrate were resolved by agarose gel electrophoresis (1% agarose gels). Cleaved and uncleaved DNA are easily visualized under ultraviolet light after staining the gel with 0.5 μg/mL of ethidium bromide. Quantitation of the reaction products for kinetic analysis were performed by densitometry measurements.

A second method involves direct measurement of the incorporation of [$^3$H]-CH$_3$ from [$^3$H]-SAM into DNA. A typical assay consists of 250 nM CcrM, 5 μM DNA (hemi- or unmethylated) and 6 μM [$^3$H]-SAM in the appropriate reaction buffer. 5 μL aliquots of the reaction are quenched in solution containing 500 μL 10% perchloric acid, 200 μL saturated potassium pyrophosphate, and 20 L 1 mg/mL singlestranded DNA at times ranging from 15 seconds to 30 minutes. The quenched samples are placed on ice for 30 minutes to precipitate all DNA. The precipitated DNA is then recovered by filtration using glass fiber filters and washed, first with cold 0.1 N HCl (five times with 1.5 mL) and;then with cold 95% ethanol (four times with 1.5 mL). The filters are then dried at 90° C. for 10 minutes and counted by standard liquid scintillation techniques. The specific activity of the reaction is determined by measuring the counts per minute present in a fixed quantity of the original reaction in the absence of washing.

Specific activity (SA) was determined by measuring the CPMs present in 5 μL of original reaction. SA=CPMs/pmol SAM. The amount of methyl incorporation was determined as follows:

$$\frac{(CPM_{Sample} - CPM_{zero})}{\text{Specific Activity}} = \text{pmol product}$$

The amount of methyl incorporation into the DNA substrate is determined by dividing the counts per minute of the washed reaction samples by the specific activity of the total reaction mixture. This yields product formation in terms of mole quantities. All data are corrected for nonspecific binding of [$^3$H]-SAM to the washed filter.

Alternatively, following the enzymatic incorporation of [$^3$H]-CH$_3$ from [$^3$H]-SAM into DNA, a 5 μl aliquot of the reaction is spotted at variable times onto DES anion-exchange filter paper. The filters are then washed 3 times for 10 minutes with 200 mL 0.3 M ammonium formate, pH 8 to remove unreacted [$^3$H]-SAM. The filters are then briefly washed twice with 95% ethanol and then washed once with anhydrous ether. The filters are then air dried and counted by standard liquid scintillation techniques. The specific activity of the reaction is determined by measuring the radioactivity present in 5 μl of the reaction spotted on glass filter fibers without washing. The amount of methyl incorporation into the DNA substrate is determined by diving the counts per minute of the washed samples by the specific activity of the total reaction mixture, yielding product formation in terms of pmol quantities. all data are corrected for nonspecific binding of [$^3$H]-SAM to the washed filter.

During the course of performing the above assays, it was observed that: the $N^6$-23/30-mer $N^6$45/50-mer, and the $N^6$-60/66-mer are preferred substrates by ratios of 10:1 and 2:1; the tested methyltransferases are processive under the assay conditions used; optimal activity was at 30° C. rather than 37° C.; and the tested enzymes are DNA-dependent (i.e., they become inactivated in the solutions used after about 20 minutes in the absence of DNA substrate). The toss of activity in the absence of a substrate does not appear to involve proteolytic degradation.

C. In Vivo Assay

A single colony of BL21(DE3) or DH5α hosting pCS255b was used to inoculate a 5 mL SB/amp (200 μg/ml) overnight culture at 37° C. The BL21(DE3) culture was divided into two aliquots at OD$_{600}$-1. One aliquot was induced with 1 mM IPTG at 37° C. overnight while the other was allowed to grow without induction. Cell cultures were centrifuged, from which cell pellets were subjected to mini plasmid prep. The recovered plasmids from DH5α and BL21(DE3) (with and without IPTG induction) were digested with: HinfI and the restriction digests were analyzed by 1% agarose gels. In all cases, controls containing the undigested plasmid were included. Plasmid recovered from DH5α was susceptible to HinfI digestion while plasmids from BL21 (DE3) with and without induction were resistant to HinfI digestion. It appears that even uninduced BL21(DE3) expresses ccrM. To ascertain that BL21(DE3) did not have intrinsic methyltransferase specific for the GANTC sites, pUC18 was introduced into BL21(DE3). pUC18 recovered from BL21(DE3) was susceptible to HinfI digestion, thereby excluding the possibility of BL21(DE3) host cells containing intrinsic M. HinfI methyltransferase activity.

Although the foregoing invention has been described in some detail by way of illustration and example for purposes of clarity of understanding, it will be obvious that certain changes and modifications may be practiced within the scope of the appended claims. All publications, patents and patent applications mentioned in this specification are hereby incorporated by reference for all purposes, to the same extent as if each individual publication, patent or patent application had been specifically and individually indicated to be incorporated by reference.

TABLE 1

Alignment of the Agrobacterium tumefaciens(At),
Brucella abortus (Ba) Rhizobium meliloti (Rm).
Caulobacter crescentus (Cc) and Helicobacter pylori (Hp)
CCrM DNA methyltransferase homologs

```
At                         IFADPPYNLQLGGNVHRP
Ba  MSLVRLAHELPIEAPRTAWLDSIIKGDCVSALERLPDHSVUVIFADPPYNLQLCGDLHRP
Rm  MSSVVSLAEISRAARPLNWLDSIIKGDCVAALNALPDHSVDVVFADPPYNLQLGGTLHRP
Cc       MKFGPETIIHGDCIEQMNALPEKSVDLIFADPPYNLQLGGDLLRP
hp       MDFLKENLNTIIEGDCLEKLKDFPNKSVDFIFADPPYFMQTEGELKRF
         ::**.***:   ::  :*::***.:****** :*   * :  *

At  DQSLVDAVDDEWDQFASFDAYDAFTRAWLLACRRVLKPNGTIWVIGSYHNIFRVGAMLQN
Ba  DQSMVSAVDDHWDQFESFQAYDAFTRAWLLACRRVLKPNGTIWVIGSYHNIFRVGTQLQD
Rm  DQSLVDAVDDDWDQFASFEAYDAFTRAWLLACRRVLKPTGTLWVIGSYHNIFRVGAILQD
Cc  DNSKVDAVDDHWDQFESFAAYDKFTREWLKAARRVLKDDGAIWVIGSYHNIFRVGVAVQD
Hp  EGTKFQGVEDHWDKFGSFEEYDTFCLQWLKECQRILKDNGSICVIGSFQNIFRIGFHLQN
    :  :  ...*:*.**:* **  ** *   **  .:*:** *::  ****::****:*   :*:

At  LDFWILN
Ba  LGFWLLNDIVWRKTNPMPNFRGRRFQNAHETLIWASREQKGKGYTFNYEAMKAANDDVQM
Rm  LHFWVLNDIIWRKTQPDAELQGRRFQNAHETLIWATANAKAKGYTFNYEAMKAANDDVQM
Cc  LGFWILNDIVWRKSNPMPNFKGTRFANAHETLIWASKSQNAKRYTFNYDALKMANDEVQM
Hp  LGFWILNDIVWYKSNPVPNFAGKRLCNAHETLIWCAKHKNNK-VTFNYKTMKYLNNNKQE
    * **:****:* *::*  .:: * *:  ********.:    : *   ****.::* *::  *

Ba  RSDWLFPICTGSERLKDENGDKVHPTQKPEALLARIMMASSKPGDVILDPFFGSGTTGAV
Rm  RSDWLFPICSGSERLKGDDGKKVHPTQKPEALLYRIMASTKPGDVILDPFFGSGTTGAV
Cc  RSDWTIPLCTGEERIKGADGQKAHPTQKPEALLYRVILSTTKPGDVILDPFFGVGTTGAA
Hp  KSVWQIPICMGNERLKDAQGKKVHSTQKPEALLKKIILSATKPKDIILDPFFGTGTTGAV
    :*:*  *.**:*.   :*.*.*.********  :::::::::** *::****** *****.

Ba  AKRLGRHFVGIEREQPYIDAATARINAVEPLGKAELTVMTGKRAEPRVAFTSVMEAGLLR
Rm  AKRLGRHFVGIEREQDYIDAAAERIAAVEPLGKATLSVMTGKKAEPRVAFNTLVESGLIK
Cc  AKRLGRKFIGIEREAEYLEHAKARIAKVVPIAPEDLDVMGSKRAEPRVPFGTIVEAGLLS
Hp  AKSMNRYFIGIEKDSFYIKEAAKRLNSTRDKS-DFITNLDLETKPPKIPMSLLISKQLLK
    **  :.*  *:***::    *:.  *  *:  .    .    :  :    *::.: ::. *:

Ba  PGTVLCDERRRFAAIVRADGTLTAN-GEAGSIHRIGARVQGFDACNGWTFWHFEENGVLK
Rm  PGTVLTDAKRRYSAIVRADGTLASG-GEAGSIHRLGAKVQGLDACNGWTFWHFEEGSVLK
Cc  PGDTLYCSKGTHVAKVRPDGSITVG-DLSGSIHKIGALVQSAPACNGWTYWHFKTDAGLA
Hp  IGDFLYSSNKEKICQVLENGQVRDNENYETSIHKMSAKYLNKTNHNGWKFFYAYYQNQFL
    *   *    .    .*  :* :   . .   ***::.*   .   ***.:::          :

Ba  PIDALRKIIREQMAAAGA
Rm  PIDELRSVIRNDLAKLN
Cc  PIDVLRAQVRAGMN
Hp  LLDELRYICQRDS
        :* **    :
```

Note:
*indicates the identical residue is present in all five saquences
: or . indicates tha amino acid at that position is conserved in all sequences.

---

What is claimed is:

1. An isolated DNA adenine methyltransferase wherein said methyltransferase has an amino acid sequence as set forth in SEQ ID No. 6.

2. An isolated nucleic acid that encodes a *Helicobacter pylori* DNA methyltansferase having an amino acid sequence comprising.

3. An isolated nucleic acid of claim 2, wherein the nucleic acid comprises SEQ ID NO:7.

4. A nucleic acid of claim 2 contained in a genetically engineered cell.

5. An isolated DNA adenine methyltransferase having an amino acid sequence as set forth in SEQ ID NO: 8.

* * * * *

UNITED STATES PATENT AND TRADEMARK OFFICE
CERTIFICATE OF CORRECTION

| | |
|---|---|
| PATENT NO. | : 6,413,751 B1 |
| APPLICATION NO. | : 09/269137 |
| DATED | : July 2, 2002 |
| INVENTOR(S) | : Benkovic et al. |

It is certified that error appears in the above-identified patent and that said Letters Patent is hereby corrected as shown below:

Please delete the paragraph at column 1, lines 10-12, and replace it with the following paragraph:

-- This invention was made with government support under Grant No. GM051426, awarded by the National Institutes of Health and Contract No. MDA72-97-1-0008, awarded by DARPA. The Government has certain rights in the invention. --

Signed and Sealed this

Twenty-second Day of December, 2009

David J. Kappos
*Director of the United States Patent and Trademark Office*

UNITED STATES PATENT AND TRADEMARK OFFICE
CERTIFICATE OF CORRECTION

PATENT NO. : 6,413,751 B1 Page 1 of 1
APPLICATION NO. : 09/269137
DATED : July 2, 2002
INVENTOR(S) : Benkovic et al.

It is certified that error appears in the above-identified patent and that said Letters Patent is hereby corrected as shown below:

Please delete the paragraph at column 1, lines 10-12, and replace it with the following paragraph:

-- This invention was made with government support under Grant No. GM051426, awarded by the National Institutes of Health and Contract No. MDA972-97-1-0008, awarded by DARPA. The Government has certain rights in the invention. --

Signed and Sealed this

Sixteenth Day of February, 2010

David J. Kappos
*Director of the United States Patent and Trademark Office*

SEQUENCE LISTING

<160> NUMBER OF SEQ ID NOS: 24

<210> SEQ ID NO 1
<211> LENGTH: 1698
<212> TYPE: DNA
<213> ORGANISM: Rhizobium meliloti
<220> FEATURE:
<221> NAME/KEY: CDS
<222> LOCATION: (304)..(1431)

<400> SEQUENCE: 1

```
gcagtgatgg cggcctgggc tgcaagctcc gtccgtgtca gcgcctggcc gcccatcaga      60
gcgggcagca tgtttgcgcg tgcgggatcg ccgatcaacg agccgatcag agctatgtcc     120
gggccttcct tcatacttcg atgataatcg aagtatcgcg gacgggcaag acccggatcg     180
```

-continued

```
gcggcgcctg acgatgact cctgcggcga cgcaaatttt tccggcgcct tcaggctttg      240
gtaaccatct tcggtaacca taagcctatc gtcagtccga gtaagcgtat ttgcgagttg      300 cca atg tca tca gtt gtt tcg ctt gcc gaa atc tcc cgt gcc gcc cgt       348
    Met Ser Ser Val Val Ser Leu Ala Glu Ile Ser Arg Ala Ala Arg
    1               5                   10                  15 ccg ctg aac tgg ctg gac agc atc atc aag gga gat tgc gtg gcc gcg       396
Pro Leu Asn Trp Leu Asp Ser Ile Ile Lys Gly Asp Cys Val Ala Ala
                20                  25                  30 ctg aac gcg ctt ccc gat cat tcg gtc gat gtc gtc ttc gcc gac ccg       444
Leu Asn Ala Leu Pro Asp His Ser Val Asp Val Val Phe Ala Asp Pro
            35                  40                  45 ccc tat aat ctt cag ctc ggc ggc acg ttg cac cgg ccc gat cag tcg       492
Pro Tyr Asn Leu Gln Leu Gly Gly Thr Leu His Arg Pro Asp Gln Ser
        50                  55                  60 ctg gtc gat gca gtg gac gac gat tgg gac cag ttt gct tcc ttc gaa       540
Leu Val Asp Ala Val Asp Asp Asp Trp Asp Gln Phe Ala Ser Phe Glu
    65                  70                  75 gcc tat gac gct ttc acc cgc gcc tgg ctg ctt gcc tgc cgg cgt gtc       588
Ala Tyr Asp Ala Phe Thr Arg Ala Trp Leu Leu Ala Cys Arg Arg Val
80                  85                  90                  95 ctg aag ccc acc ggc acg ctc tgg gtc atc ggt tcc tac cac aat atc       636
Leu Lys Pro Thr Gly Thr Leu Trp Val Ile Gly Ser Tyr His Asn Ile
                100                 105                 110 ttc cgg gtc ggc gcg atc ctc cag gac ctg cac ttc tgg gtc ttg aac       684
Phe Arg Val Gly Ala Ile Leu Gln Asp Leu His Phe Trp Val Leu Asn
            115                 120                 125 gat atc atc tgg cgc aag acc caa ccc gat gcc gaa ctt caa ggg cgc       732
Asp Ile Ile Trp Arg Lys Thr Gln Pro Asp Ala Glu Leu Gln Gly Arg
        130                 135                 140 cgc ttc cag aac gcg cat gaa acg ctg atc tgg gcg acg gcg aac gcc       780
Arg Phe Gln Asn Ala His Glu Thr Leu Ile Trp Ala Thr Ala Asn Ala
    145                 150                 155 aag gcc aag ggt tat acc ttc aac tac gaa gcg atg aag gcg gcg aac       828
Lys Ala Lys Gly Tyr Thr Phe Asn Tyr Glu Ala Met Lys Ala Ala Asn
160                 165                 170                 175 gac gac gtt cag atg cgc tcc gac tgg ctg ttc ccc atc tgc tcc ggt       876
Asp Asp Val Gln Met Arg Ser Asp Trp Leu Phe Pro Ile Cys Ser Gly
                180                 185                 190 tcc gag cgg ctg aag ggc gac gac ggc aag aaa gta cac ccg acg caa       924
Ser Glu Arg Leu Lys Gly Asp Asp Gly Lys Lys Val His Pro Thr Gln
            195                 200                 205 aag ccg gaa gcg ctg ctt gcc cgc atc ctg atg gcc tcg acc aag ccc       972
Lys Pro Glu Ala Leu Leu Ala Arg Ile Leu Met Ala Ser Thr Lys Pro
        210                 215                 220 ggg gac gtc gtg ctt gat ccg ttc ttc ggc tcc ggc acc acc ggg gcg      1020
Gly Asp Val Val Leu Asp Pro Phe Phe Gly Ser Gly Thr Thr Gly Ala
    225                 230                 235 gtc gcc aag cgc ctc ggc cgg cac ttc gtc ggg atc gag cgc gag cag      1068
Val Ala Lys Arg Leu Gly Arg His Phe Val Gly Ile Glu Arg Glu Gln
240                 245                 250                 255 gac tat atc gat gcc gcc gcc gaa cgt atc gcg gcc gtg gag ccg ctc      1116
Asp Tyr Ile Asp Ala Ala Ala Glu Arg Ile Ala Ala Val Glu Pro Leu
                260                 265                 270 ggc aag gcc acg ctc tcg gtc atg acc ggc aag aag gcg gag ccg cgc      1164
Gly Lys Ala Thr Leu Ser Val Met Thr Gly Lys Lys Ala Glu Pro Arg
            275                 280                 285 gtc gcc ttc aac act ctg gtg gaa agc ggg ctc atc aag ccc ggc acg      1212
Val Ala Phe Asn Thr Leu Val Glu Ser Gly Leu Ile Lys Pro Gly Thr
```

-continued

```
                290                 295                 300
gtt ctg acg gat gcg aag cgc cgc tac agc gcg atc gtc cgc gcc gac    1260
Val Leu Thr Asp Ala Lys Arg Arg Tyr Ser Ala Ile Val Arg Ala Asp
    305                 310                 315 ggc acg ctg gcg tcc ggc ggc gag gct gga tcc att cac cgc ctc ggc    1308
Gly Thr Leu Ala Ser Gly Gly Glu Ala Gly Ser Ile His Arg Leu Gly
320                 325                 330                 335 gca aaa gtg cag ggc ctc gac gcc tgc aac ggc tgg acc ttc tgg cac    1356
Ala Lys Val Gln Gly Leu Asp Ala Cys Asn Gly Trp Thr Phe Trp His
                340                 345                 350 ttc gag gag gga agc gta ttg aaa ccg atc gac gag ctc aga tcc gtc    1404
Phe Glu Glu Gly Ser Val Leu Lys Pro Ile Asp Glu Leu Arg Ser Val
            355                 360                 365 att cga aac gac ctg gca aaa ctg aac tgatcaacca gttccgcctg          1451
Ile Arg Asn Asp Leu Ala Lys Leu Asn
        370                 375 ggtcttcgat aggcgcccccc ttccggtttt tgtgccttca gtcccggatg agcgctttaa  1511
acgccggaat ccgaagagga ttccggggct ttgtatcaat gcggggcgtc agcgttacag  1571
catggcagcc gctgccagga gggtgccgcg tccgaagctg ataccgtag ccgcgagatc   1631 ggctttcagc ctttcggcgc cggtgaactg aaccgcgtgc cagccggccg ctgcgcgcct  1691
tcgacat                                                             1698
```

<210> SEQ ID NO 2
<211> LENGTH: 376
<212> TYPE: PRT
<213> ORGANISM: Rhizobium meliloti

<400> SEQUENCE: 2

```
Met Ser Ser Val Val Ser Leu Ala Glu Ile Ser Arg Ala Ala Arg Pro
  1               5                  10                  15

Leu Asn Trp Leu Asp Ser Ile Ile Lys Gly Asp Cys Val Ala Ala Leu
             20                  25                  30

Asn Ala Leu Pro Asp His Ser Val Asp Val Val Phe Ala Asp Pro Pro
         35                  40                  45

Tyr Asn Leu Gln Leu Gly Gly Thr Leu His Arg Pro Asp Gln Ser Leu
     50                  55                  60

Val Asp Ala Val Asp Asp Trp Asp Gln Phe Ala Ser Phe Glu Ala
 65                  70                  75                  80

Tyr Asp Ala Phe Thr Arg Ala Trp Leu Leu Ala Cys Arg Arg Val Leu
                 85                  90                  95

Lys Pro Thr Gly Thr Leu Trp Val Ile Gly Ser Tyr His Asn Ile Phe
            100                 105                 110

Arg Val Gly Ala Ile Leu Gln Asp Leu His Phe Trp Val Leu Asn Asp
        115                 120                 125

Ile Ile Trp Arg Lys Thr Gln Pro Asp Ala Glu Leu Gln Gly Arg Arg
130                 135                 140

Phe Gln Asn Ala His Glu Thr Leu Ile Trp Ala Thr Ala Asn Ala Lys
145                 150                 155                 160

Ala Lys Gly Tyr Thr Phe Asn Tyr Glu Ala Met Lys Ala Ala Asn Asp
                165                 170                 175

Asp Val Gln Met Arg Ser Asp Trp Leu Phe Pro Ile Cys Ser Gly Ser
            180                 185                 190

Glu Arg Leu Lys Gly Asp Asp Gly Lys Lys Val His Pro Thr Gln Lys
        195                 200                 205
```

-continued

```
Pro Glu Ala Leu Leu Ala Arg Ile Leu Met Ala Ser Thr Lys Pro Gly
    210                 215                 220

Asp Val Val Leu Asp Pro Phe Phe Gly Ser Gly Thr Thr Gly Ala Val
225                 230                 235                 240
Ala Lys Arg Leu Gly Arg His Phe Val Gly Ile Glu Arg Glu Gln Asp
                245                 250                 255

Tyr Ile Asp Ala Ala Ala Glu Arg Ile Ala Ala Val Glu Pro Leu Gly
            260                 265                 270
Lys Ala Thr Leu Ser Val Met Thr Gly Lys Lys Ala Glu Pro Arg Val
        275                 280                 285
Ala Phe Asn Thr Leu Val Glu Ser Gly Leu Ile Lys Pro Gly Thr Val
    290                 295                 300
Leu Thr Asp Ala Lys Arg Arg Tyr Ser Ala Ile Val Arg Ala Asp Gly
305                 310                 315                 320
Thr Leu Ala Ser Gly Gly Glu Ala Gly Ser Ile His Arg Leu Gly Ala
                325                 330                 335
Lys Val Gln Gly Leu Asp Ala Cys Asn Gly Trp Thr Phe Trp His Phe
            340                 345                 350

Glu Glu Gly Ser Val Leu Lys Pro Ile Asp Glu Leu Arg Ser Val Ile
        355                 360                 365
Arg Asn Asp Leu Ala Lys Leu Asn
    370                 375

<210> SEQ ID NO 3
<211> LENGTH: 1731
<212> TYPE: DNA
<213> ORGANISM: Brucella abortus
<220> FEATURE:
<221> NAME/KEY: CDS
<222> LOCATION: (394)..(1524)

<400> SEQUENCE: 3
aaagggtacg aacagcaccc tcaaatatcg attatgacgc aactccgcga aattcattat      60
caaactacac ccgacaggca cttcagtctg cgagcggctg ccacacacac tgcatcatcg     120
tcatttgccg ccggatcata gaccaaaaga aataaccaag ccttattgat tgcgacatat     180
gccgttccag ccttgcacat ggatcacgtc gtcacgatga caagtcgata attatctctg     240
ccttattggg cgcgcaaagg ccgcaaagcc gggctttccc tgtgatatta agaaaagatt     300
tacgatttca agcacttggc gttaagcgca tatttaccct acgcagtaac cataggaaca     360 agtttttgc gttcacaggt aatcgagtat ccc atg tcc cta gta cgt ctt gcg      414
                                     Met Ser Leu Val Arg Leu Ala
                                       1               5 cat gag ttg ccc atc gag gcc ccg cgt acc gcc tgg ctc gac tcc atc      462
His Glu Leu Pro Ile Glu Ala Pro Arg Thr Ala Trp Leu Asp Ser Ile
        10                  15                  20 atc aaa ggt gat tgc gtt tcc gcg ctg gag cgc ctg ccg gat cat tcc      510
Ile Lys Gly Asp Cys Val Ser Ala Leu Glu Arg Leu Pro Asp His Ser
    25                  30                  35 gta gac gtc atc ttt gcc gat ccg ccc tat aat ctc cag ctt ggc ggc      558
Val Asp Val Ile Phe Ala Asp Pro Pro Tyr Asn Leu Gln Leu Gly Gly
 40                  45                  50                  55 gat ctg cac cgt ccg gat cag tcc atg gtc agc gcc gtg gac gat cat      606
Asp Leu His Arg Pro Asp Gln Ser Met Val Ser Ala Val Asp Asp His
                60                  65                  70 tgg gac cag ttt gaa agc ttc cag gcc tat gac gcc ttc acc cgc gcc      654
Trp Asp Gln Phe Glu Ser Phe Gln Ala Tyr Asp Ala Phe Thr Arg Ala
            75                  80                  85
```

```
tgg ctg ctc gcc tgc cgc gtg ctg aag ccg aat ggc acc atc tgg        702
Trp Leu Leu Ala Cys Arg Arg Val Leu Lys Pro Asn Gly Thr Ile Trp
         90                  95                 100 gtc atc ggt tcc tat cac aat att ttc cgc gtc ggc acg cag ttg cag    750
Val Ile Gly Ser Tyr His Asn Ile Phe Arg Val Gly Thr Gln Leu Gln
        105                 110                 115 gat ctg ggc ttc tgg ctc ctc aac gac att gtc tgg cgc aag acc aat    798
Asp Leu Gly Phe Trp Leu Leu Asn Asp Ile Val Trp Arg Lys Thr Asn
120                 125                 130                 135 ccc atg ccg aat ttc cgt ggc cgc gtt ttc cag aat gcg cat gaa acg    846
Pro Met Pro Asn Phe Arg Gly Arg Arg Phe Gln Asn Ala His Glu Thr
                140                 145                 150 ctg atc tgg gct tcg cgt gag cag aag ggc aag gga tat act ttc aat    894
Leu Ile Trp Ala Ser Arg Glu Gln Lys Gly Lys Gly Tyr Thr Phe Asn
            155                 160                 165 tac gag gcc atg aaa gcg gcc aat gac gat gtg cag atg cgt tcg gac    942
Tyr Glu Ala Met Lys Ala Ala Asn Asp Asp Val Gln Met Arg Ser Asp
        170                 175                 180 tgg ctg ttc ccg atc tgc acc ggc agt gaa cgc ctg aag gac gag aac    990
Trp Leu Phe Pro Ile Cys Thr Gly Ser Glu Arg Leu Lys Asp Glu Asn
185                 190                 195 ggc gac aag gtc cac ccg acc cag aag ccg gaa gca ctt ctc gcg cgc   1038
Gly Asp Lys Val His Pro Thr Gln Lys Pro Glu Ala Leu Leu Ala Arg
200                 205                 210                 215 atc atg atg gct tca agc aag ccg ggc gac gtt att ctc gac cca ttc   1086
Ile Met Met Ala Ser Ser Lys Pro Gly Asp Val Ile Leu Asp Pro Phe
                220                 225                 230 ttc ggt tcc ggc acg acc ggc gcg gtc gcc aag cgg ctt ggc cgc cat   1134
Phe Gly Ser Gly Thr Thr Gly Ala Val Ala Lys Arg Leu Gly Arg His
            235                 240                 245 ttc gtc ggc atc gag cgt gaa cag ccc tat atc gac gcc gca acc gcc   1182
Phe Val Gly Ile Glu Arg Glu Gln Pro Tyr Ile Asp Ala Ala Thr Ala
        250                 255                 260 cgc atc aat gcc gtg gag ccg ctt ggc aag gcg gaa ctc acg gtg atg   1230
Arg Ile Asn Ala Val Glu Pro Leu Gly Lys Ala Glu Leu Thr Val Met
265                 270                 275 acc ggc aag cgc gca gag ccg cgc gtg gcc ttc acg agc gta atg gaa   1278
Thr Gly Lys Arg Ala Glu Pro Arg Val Ala Phe Thr Ser Val Met Glu
280                 285                 290                 295 gcg ggc ctt ttg cgt ccg gga acc gtg ctt tgt gat gaa cgc cgc cgt   1326
Ala Gly Leu Leu Arg Pro Gly Thr Val Leu Cys Asp Glu Arg Arg Arg
                300                 305                 310 ttt gcc gcc att gtt cgc gcc gat ggg acg ctg acg gcc aac ggc gaa   1374
Phe Ala Ala Ile Val Arg Ala Asp Gly Thr Leu Thr Ala Asn Gly Glu
            315                 320                 325 gcc ggt tca atc cat cgt att ggc gcc agg gtt caa ggg ttc gat gcc   1422
Ala Gly Ser Ile His Arg Ile Gly Ala Arg Val Gln Gly Phe Asp Ala
        330                 335                 340 tgc aat ggc tgg acc ttc tgg cac ttt gag gaa aac ggc gta ctg aag   1470
Cys Asn Gly Trp Thr Phe Trp His Phe Glu Glu Asn Gly Val Leu Lys
345                 350                 355 cct atc gat gcc ctg cgc aag atc atc cgc gaa cag atg gct gcg gca   1518
Pro Ile Asp Ala Leu Arg Lys Ile Ile Arg Glu Gln Met Ala Ala Ala
                360                 365                 370                 375 ggt gca taagaaagtt taatatcgga cgatctccag taaagtctga tagcaaggcg   1574
Gly Ala ctcgaagttt tcaaacttcg ggcgccttca ttctttcaga aagaaagctg tcgcgcccgc   1634
aaatcgtcgg ccagtttggc tgcgctggta aaatgcaccg cctgccagcc cgcttgcttc   1694
```

```
gcaccttcca cattgtgcat cgtgtcatcg atgaaga                    1731
```

<210> SEQ ID NO 4
<211> LENGTH: 377
<212> TYPE: PRT
<213> ORGANISM: Brucella abortus

<400> SEQUENCE: 4

```
Met Ser Leu Val Arg Leu Ala His Glu Leu Pro Ile Glu Ala Pro Arg
 1               5                  10                  15

Thr Ala Trp Leu Asp Ser Ile Ile Lys Gly Asp Cys Val Ser Ala Leu
            20                  25                  30

Glu Arg Leu Pro Asp His Ser Val Asp Val Ile Phe Ala Asp Pro Pro
        35                  40                  45

Tyr Asn Leu Gln Leu Gly Gly Asp Leu His Arg Pro Asp Gln Ser Met
    50                  55                  60

Val Ser Ala Val Asp Asp His Trp Asp Gln Phe Glu Ser Phe Gln Ala
 65                  70                  75                  80

Tyr Asp Ala Phe Thr Arg Ala Trp Leu Leu Ala Cys Arg Arg Val Leu
                85                  90                  95

Lys Pro Asn Gly Thr Ile Trp Val Ile Gly Ser Tyr His Asn Ile Phe
            100                 105                 110

Arg Val Gly Thr Gln Leu Gln Asp Leu Gly Phe Trp Leu Leu Asn Asp
        115                 120                 125

Ile Val Trp Arg Lys Thr Asn Pro Met Pro Asn Phe Arg Gly Arg Arg
    130                 135                 140

Phe Gln Asn Ala His Glu Thr Leu Ile Trp Ala Ser Arg Glu Gln Lys
145                 150                 155                 160

Gly Lys Gly Tyr Thr Phe Asn Tyr Glu Ala Met Lys Ala Ala Asn Asp
                165                 170                 175

Asp Val Gln Met Arg Ser Asp Trp Leu Phe Pro Ile Cys Thr Gly Ser
            180                 185                 190

Glu Arg Leu Lys Asp Glu Asn Gly Asp Lys Val His Pro Thr Gln Lys
        195                 200                 205

Pro Glu Ala Leu Leu Ala Arg Ile Met Met Ala Ser Ser Lys Pro Gly
    210                 215                 220

Asp Val Ile Leu Asp Pro Phe Phe Gly Ser Gly Thr Thr Gly Ala Val
225                 230                 235                 240

Ala Lys Arg Leu Gly Arg His Phe Val Gly Ile Glu Arg Glu Gln Pro
                245                 250                 255

Tyr Ile Asp Ala Ala Thr Ala Arg Ile Asn Ala Val Glu Pro Leu Gly
            260                 265                 270

Lys Ala Glu Leu Thr Val Met Thr Gly Lys Arg Ala Glu Pro Arg Val
        275                 280                 285

Ala Phe Thr Ser Val Met Glu Ala Gly Leu Leu Arg Pro Gly Thr Val
    290                 295                 300

Leu Cys Asp Glu Arg Arg Arg Phe Ala Ala Ile Val Arg Ala Asp Gly
305                 310                 315                 320

Thr Leu Thr Ala Asn Gly Glu Ala Gly Ser Ile His Arg Ile Gly Ala
                325                 330                 335

Arg Val Gln Gly Phe Asp Ala Cys Asn Gly Trp Thr Phe Trp His Phe
            340                 345                 350

Glu Glu Asn Gly Val Leu Lys Pro Ile Asp Ala Leu Arg Lys Ile Ile
        355                 360                 365
```

```
Arg Glu Gln Met Ala Ala Ala Gly Ala
    370                 375
```

<210> SEQ ID NO 5
<211> LENGTH: 255
<212> TYPE: DNA
<213> ORGANISM: Agrobacterium tumefaciens
<220> FEATURE:
<221> NAME/KEY: CDS
<222> LOCATION: (1)..(255)

<400> SEQUENCE: 5

```
att ttc gcc gat ccg ccg tat aat ctc cag ctt ggc ggc aac gtg cac      48
Ile Phe Ala Asp Pro Pro Tyr Asn Leu Gln Leu Gly Gly Asn Val His
 1               5                  10                  15 cgg ccc gat cag tcg ctg gtc gat gcc gtt gat gac gaa tgg gac cag      96
Arg Pro Asp Gln Ser Leu Val Asp Ala Val Asp Asp Glu Trp Asp Gln
            20                  25                  30 ttc gcc tcc ttc gac gcc tat gac gcc ttc acc cgc gcc tgg ctg ctc     144
Phe Ala Ser Phe Asp Ala Tyr Asp Ala Phe Thr Arg Ala Trp Leu Leu
        35                  40                  45 gcc tgc cgc cgt gtg ctg aaa ccg aac ggc acc atc tgg gtc atc ggc     192
Ala Cys Arg Arg Val Leu Lys Pro Asn Gly Thr Ile Trp Val Ile Gly
    50                  55                  60 tcc tat cac aat atc ttc cgc gtc ggc gcc atg ctc cag aac ctc gat     240
Ser Tyr His Asn Ile Phe Arg Val Gly Ala Met Leu Gln Asn Leu Asp
65                  70                  75                  80 ttc tgg atc ctc aac                                                 255
Phe Trp Ile Leu Asn
                85
```

<210> SEQ ID NO 6
<211> LENGTH: 85
<212> TYPE: PRT
<213> ORGANISM: Agrobacterium tumefaciens

<400> SEQUENCE: 6

```
Ile Phe Ala Asp Pro Pro Tyr Asn Leu Gln Leu Gly Gly Asn Val His
 1               5                  10                  15

Arg Pro Asp Gln Ser Leu Val Asp Ala Val Asp Asp Glu Trp Asp Gln
            20                  25                  30

Phe Ala Ser Phe Asp Ala Tyr Asp Ala Phe Thr Arg Ala Trp Leu Leu
        35                  40                  45

Ala Cys Arg Arg Val Leu Lys Pro Asn Gly Thr Ile Trp Val Ile Gly
    50                  55                  60

Ser Tyr His Asn Ile Phe Arg Val Gly Ala Met Leu Gln Asn Leu Asp
65                  70                  75                  80

Phe Trp Ile Leu Asn
                85
```

<210> SEQ ID NO 7
<211> LENGTH: 2093
<212> TYPE: DNA
<213> ORGANISM: Helicobacter pylori
<220> FEATURE:
<221> NAME/KEY: CDS
<222> LOCATION: (202)..(1278)

<400> SEQUENCE: 7

```
aacgggcatg ctttgcgatt tgcatttgaa cggatcgggg agttatgcgt ttttgttgta     60
tcgtttaaaa taggtgggga taggtagctt ctatcatttg atgcatttga tgagaacaaa    120
```

-continued

```
gctagggact aaacattaag atagccttaa aacgcttgtg ttaaaatggc cagagtagca         180
gatataaaag gctagttaat c atg gat ttt tta aaa gaa aac tta aac act          231
                       Met Asp Phe Leu Lys Glu Asn Leu Asn Thr
                         1               5                  10 atc ata gag ggg gat tgt tta gaa aaa ttg aaa gat ttt cct aat aaa          279
Ile Ile Glu Gly Asp Cys Leu Glu Lys Leu Lys Asp Phe Pro Asn Lys
                15                  20                  25 agc gtt gat ttt atc ttt gct gac ccc cca tat ttt atg caa aca gag          327
Ser Val Asp Phe Ile Phe Ala Asp Pro Pro Tyr Phe Met Gln Thr Glu
            30                  35                  40 gga gaa ttg aag cgt ttt gaa ggc aca aaa ttt caa ggc gtt gag gat          375
Gly Glu Leu Lys Arg Phe Glu Gly Thr Lys Phe Gln Gly Val Glu Asp
        45                  50                  55 cat tgg gat aaa ttt ggc tct ttt gaa gaa tac gat acc ttt tgt ttg          423
His Trp Asp Lys Phe Gly Ser Phe Glu Glu Tyr Asp Thr Phe Cys Leu
    60                  65                  70 ggt tgg tta aaa gaa tgc caa agg att tta aaa gat aat ggc agt att          471
Gly Trp Leu Lys Glu Cys Gln Arg Ile Leu Lys Asp Asn Gly Ser Ile
75                  80                  85                  90 tgt gtg ata ggg agt ttt caa aat att ttt aga att ggt ttt cat ttg          519
Cys Val Ile Gly Ser Phe Gln Asn Ile Phe Arg Ile Gly Phe His Leu
                95                  100                 105 caa aat tta ggg ttt tgg ata ctc aat gat att gtt tgg tac aag agc          567
Gln Asn Leu Gly Phe Trp Ile Leu Asn Asp Ile Val Trp Tyr Lys Ser
            110                 115                 120 aat ccg gtg cct aat ttt gct ggc aag aga cta tgc aac gcc cat gaa          615
Asn Pro Val Pro Asn Phe Ala Gly Lys Arg Leu Cys Asn Ala His Glu
        125                 130                 135 acg ctt att tgg tgc gct aaa cac aaa aac aac aaa gtt acc ttt aat          663
Thr Leu Ile Trp Cys Ala Lys His Lys Asn Asn Lys Val Thr Phe Asn
    140                 145                 150 tat aaa aca atg aag tac ctc aat aac aat aaa caa gaa aaa tcg gtt          711
Tyr Lys Thr Met Lys Tyr Leu Asn Asn Asn Lys Gln Glu Lys Ser Val
155                 160                 165                 170 tgg caa atc cct att tgc atg ggt aac gaa agg cta aaa gac gcg caa          759
Trp Gln Ile Pro Ile Cys Met Gly Asn Glu Arg Leu Lys Asp Ala Gln
                175                 180                 185 ggt aaa aaa gtg cat tcc acg caa aaa cca gaa gcg ctc tta aaa aaa          807
Gly Lys Lys Val His Ser Thr Gln Lys Pro Glu Ala Leu Leu Lys Lys
            190                 195                 200 atc att tta agc gcg act aaa cct aaa gac att att tta gat ccc ttt          855
Ile Ile Leu Ser Ala Thr Lys Pro Lys Asp Ile Ile Leu Asp Pro Phe
        205                 210                 215 ttt ggc aca ggc aca aca ggg gct gtg gct aaa tcc atg aac agg tat          903
Phe Gly Thr Gly Thr Thr Gly Ala Val Ala Lys Ser Met Asn Arg Tyr
    220                 225                 230 ttt att ggc att gaa aaa gat tct ttt tat atc aaa gaa gcg gca aaa          951
Phe Ile Gly Ile Glu Lys Asp Ser Phe Tyr Ile Lys Glu Ala Ala Lys
235                 240                 245                 250 cgc ctt aat agc act agg gat aaa agc gat ttt atc act aat tta gat          999
Arg Leu Asn Ser Thr Arg Asp Lys Ser Asp Phe Ile Thr Asn Leu Asp
                255                 260                 265 tta gaa act aaa ccc cca aaa atc cct atg agt ctt tta att tct aaa         1047
Leu Glu Thr Lys Pro Pro Lys Ile Pro Met Ser Leu Leu Ile Ser Lys
            270                 275                 280 caa tta ctc aaa att gga gat ttt tta tac tca tct aac aaa gaa aaa         1095
Gln Leu Leu Lys Ile Gly Asp Phe Leu Tyr Ser Ser Asn Lys Glu Lys
        285                 290                 295 att tgt caa gtt tta gaa aac gga caa gtg agg gat aat gaa aac tat         1143
```

```
                                                          -continued

Ile Cys Gln Val Leu Glu Asn Gly Gln Val Arg Asp Asn Glu Asn Tyr
                300                 305                 310 gaa act tct att cat aag atg agc gct aaa tat ttg aat aaa act aac    1191
Glu Thr Ser Ile His Lys Met Ser Ala Lys Tyr Leu Asn Lys Thr Asn
315                 320                 325                 330 cat aat ggc tgg aaa ttt ttt tat gcg tat tac caa aat caa ttt tta    1239
His Asn Gly Trp Lys Phe Phe Tyr Ala Tyr Tyr Gln Asn Gln Phe Leu
                335                 340                 345 ttg tta gat gaa ttg cgt tat atc tgc caa agg gac tct taatggacta    1288
Leu Leu Asp Glu Leu Arg Tyr Ile Cys Gln Arg Asp Ser
                350                 355 tcaaaccttt aacgagattt ttaatcgttt tgttttgga acatctaaag caaaattact   1348
tgaaaatatt gccgaaaatc ctgaacgcta tttggggatt tttagaccca ctaagcctaa   1408
gacaaaacta ttacaaaatt tattgacttc tcatgagatt aagtttggcg atgcgtttga   1468
atgcttaata gaacaatatt taaaagagca taacttttca cctttatcta aaaaaattcc   1528
ttattacaat aaggataaag aaaaaaggga atctttagaa ttagatcagt ttgctaaaaa   1588
agataacaca tattatttta tagaacaaaa aatgcgagat gaccatgaca gcaccaaaaa   1648
gagagggcaa atagataact ttgaaaggaa attagaggct ttagtccatc gttatggcga   1708
aaacattcaa ggctattttt attttataga tgagggtttg aataaaaatc aaaattacta   1768
taaagaagaa ttgcaaaaat tatctgttga ttatggcgtg cctttgagtt tgtgttatgg   1828
taaggggttg tttgaatctc ttaatatccc gcaagtttgg gatgaggttt taagccattt   1888
agtgcgatgg cgtgaaacct acccgatttt acccagtttg aattttgatg aaaatccttt   1948
agaaagtttt agagaaatca agatttagc gccaagcgtt tataggaagc ttttggataa    2008
tgatgaaatt ttcaatcttg tgttaattttt attcccagaa caaaaagttt taaaaatgtt   2068
agtagagcat tttagacaac aaaat                                        2093

<210> SEQ ID NO 8
<211> LENGTH: 359
<212> TYPE: PRT
<213> ORGANISM: Helicobacter pylori

<400> SEQUENCE: 8

Met Asp Phe Leu Lys Glu Asn Leu Asn Thr Ile Ile Glu Gly Asp Cys
 1               5                  10                  15

Leu Glu Lys Leu Lys Asp Phe Pro Asn Lys Ser Val Asp Phe Ile Phe
                20                  25                  30

Ala Asp Pro Pro Tyr Phe Met Gln Thr Glu Gly Glu Leu Lys Arg Phe
            35                  40                  45

Glu Gly Thr Lys Phe Gln Gly Val Glu Asp His Trp Asp Lys Phe Gly
        50                  55                  60

Ser Phe Glu Glu Tyr Asp Thr Phe Cys Leu Gly Trp Leu Lys Glu Cys
 65                 70                  75                  80

Gln Arg Ile Leu Lys Asp Asn Gly Ser Ile Cys Val Ile Gly Ser Phe
                85                  90                  95

Gln Asn Ile Phe Arg Ile Gly Phe His Leu Gln Asn Leu Gly Phe Trp
            100                 105                 110

Ile Leu Asn Asp Ile Val Trp Tyr Lys Ser Asn Pro Val Pro Asn Phe
        115                 120                 125

Ala Gly Lys Arg Leu Cys Asn Ala His Glu Thr Leu Ile Trp Cys Ala
    130                 135                 140

Lys His Lys Asn Asn Lys Val Thr Phe Asn Tyr Lys Thr Met Lys Tyr
```

-continued

```
                145                 150                 155                 160
Leu Asn Asn Asn Lys Gln Glu Lys Ser Val Trp Gln Ile Pro Ile Cys
                165                 170                 175

Met Gly Asn Glu Arg Leu Lys Asp Ala Gln Gly Lys Lys Val His Ser
            180                 185                 190

Thr Gln Lys Pro Glu Ala Leu Leu Lys Lys Ile Ile Leu Ser Ala Thr
        195                 200                 205

Lys Pro Lys Asp Ile Ile Leu Asp Pro Phe Phe Gly Thr Gly Thr Thr
    210                 215                 220

Gly Ala Val Ala Lys Ser Met Asn Arg Tyr Phe Ile Gly Ile Glu Lys
225                 230                 235                 240

Asp Ser Phe Tyr Ile Lys Glu Ala Ala Lys Arg Leu Asn Ser Thr Arg
                245                 250                 255

Asp Lys Ser Asp Phe Ile Thr Asn Leu Asp Leu Glu Thr Lys Pro Pro
            260                 265                 270

Lys Ile Pro Met Ser Leu Leu Ile Ser Lys Gln Leu Leu Lys Ile Gly
        275                 280                 285

Asp Phe Leu Tyr Ser Ser Asn Lys Glu Lys Ile Cys Gln Val Leu Glu
    290                 295                 300

Asn Gly Gln Val Arg Asp Asn Glu Asn Tyr Glu Thr Ser Ile His Lys
305                 310                 315                 320

Met Ser Ala Lys Tyr Leu Asn Lys Thr Asn His Asn Gly Trp Lys Phe
                325                 330                 335

Phe Tyr Ala Tyr Tyr Gln Asn Gln Phe Leu Leu Leu Asp Glu Leu Arg
            340                 345                 350

Tyr Ile Cys Gln Arg Asp Ser
        355

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Forward
      primer (IFADDPPY)

<400> SEQUENCE: 9
atyttygcbg ayccbccbta                                              20

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Forward
      primer 1 (LDPFFG)

<400> SEQUENCE: 10
ccraaraavg grtcsag                                                 17

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Forward
      primer 2 (IGIERE)

<400> SEQUENCE: 11
tcvcgytcra tvccrat                                                 17
```

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 12
actcgcgagt caacaga                                                    17

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 13
ggctatttct gttgactcgc gag                                             23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 14
tcctctcgcg agtcaacaga aat                                             23

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 15
cgcggatatt tctgttgact cgcgagagga                                      30

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide
<220> FEATURE:
<221> NAME/KEY: modified_base
<222> LOCATION: (11)
<223> OTHER INFORMATION: m2a

<400> SEQUENCE: 16
tcctctcgcg agtcaacaga aat                                             23

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide
<220> FEATURE:

```
<221> NAME/KEY: modified_base
<222> LOCATION: (18)
<223> OTHER INFORMATION: m2a

<400> SEQUENCE: 17
cgcggatatt tctgttgact cgcgagagga                              30

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 18
atcctctcgc gagtcaacag aaatatccgc tcatcaccgc aagtt             45

<210> SEQ ID NO 19
<211> LENGTH: 51
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 19
aacggataac ttgcggtgat gagcggatat ttctgttgac tcgcgagagg a      51

<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide
<220> FEATURE:
<221> NAME/KEY: modified_base
<222> LOCATION: (12)
<223> OTHER INFORMATION: m2a

<400> SEQUENCE: 20
atcctctcgc gagtcaacag aaatatccgc tcatcaccgc aagtt             45

<210> SEQ ID NO 21
<211> LENGTH: 51
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 21
aacggaaaac ttgcggtgat gagcggatat ttctgttgac tcgcgagagg a      51

<210> SEQ ID NO 22
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 22
atcctctcgc gagtcaacag aaatatccgc gagtcaccgc aagttttccg tttgaccggc  60

<210> SEQ ID NO 23
```

-continued

```
<211> LENGTH: 66
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 23
ggagggtgcc ggtcaaacgg aaaacttgcg gtgactcgcg gatatttctg ttgactcgcg      60
agagga                                                                66

<210> SEQ ID NO 24
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide
<220> FEATURE:
<221> NAME/KEY: modified_base
<222> LOCATION: (12)
<223> OTHER INFORMATION: m2a
<220> FEATURE:
<221> NAME/KEY: modified_base
<222> LOCATION: (32)
<223> OTHER INFORMATION: m2a

<400> SEQUENCE: 24
atcctctcgc gagtcaacag aaatatccgc gagtcaccgc aagttttccg tttgaccggc      60
```